(12) United States Patent
Kelly-Morgan et al.

(10) Patent No.: US 9,746,514 B2
(45) Date of Patent: Aug. 29, 2017

(54) APPARATUS AND METHOD FOR ACCURATE MEASUREMENT AND MAPPING OF FORWARD AND REVERSE-BIAS CURRENT-VOLTAGE CHARACTERISTICS OF LARGE AREA LATERAL P-N JUNCTIONS

(71) Applicant: KLA-Tencor Corporation, Milpitas, CA (US)

(72) Inventors: Ian Sierra Gabriel Kelly-Morgan, San Francisco, CA (US); Vladimir N. Faifer, Santa Clara, CA (US); James A. Real, Oakland, CA (US); Biren Salunke, San Jose, CA (US); Ralph Nyffenegger, Palo Alto, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 189 days.

(21) Appl. No.: 14/475,330

(22) Filed: Sep. 2, 2014

(65) Prior Publication Data
US 2015/0061714 A1    Mar. 5, 2015

Related U.S. Application Data

(60) Provisional application No. 61/873,545, filed on Sep. 4, 2013.

(51) Int. Cl.
*G01R 31/10* (2006.01)
*G01R 31/26* (2014.01)
(Continued)

(52) U.S. Cl.
CPC ......... *G01R 31/2648* (2013.01); *G01N 27/00* (2013.01); *H01L 22/14* (2013.01);
(Continued)

(58) Field of Classification Search
CPC    G01R 1/067; G01R 1/06788; G01R 1/06772; G01R 1/06766; G01R 1/07;
(Continued)

(56) References Cited

U.S. PATENT DOCUMENTS

| 4,812,756 A | 3/1989 | Curtis et al. |
|---|---|---|
| 5,216,362 A | 6/1993 | Verkuil |

(Continued)

OTHER PUBLICATIONS

Gang Peng et al., Detection of Nonpolar Molecules by Means of Carrier Scattering in Random Networks of Carbon Nanotubes: Toward Diagnosis of Diseases via Breath Samples, American Chemical Society, Jan. 2009, 3 pages, KP Technology Ltd, Scotland UK.

(Continued)

*Primary Examiner* — Thang Le
(74) *Attorney, Agent, or Firm* — Suiter Swantz pc llo

(57) ABSTRACT

Methods and apparatus for providing measurements in p-n junctions and taking into account the lateral current for improved accuracy are disclosed. The lateral current may be controlled, allowing the spreading of the current to be reduced or substantially eliminated. Alternatively or additionally, the lateral current may be measured, allowing a more accurate normal current to be calculated by compensating for the measured spreading. In addition, the techniques utilized for controlling the lateral current and the techniques utilized for measuring the lateral current may also be implemented jointly.

27 Claims, 33 Drawing Sheets

(51) Int. Cl.
*G01N 27/00* (2006.01)
*H01L 21/66* (2006.01)
*G01N 33/00* (2006.01)
*G01R 1/07* (2006.01)
*G01R 27/08* (2006.01)

(52) U.S. Cl.
CPC ........ *G01N 2033/0095* (2013.01); *G01R 1/07* (2013.01); *G01R 27/08* (2013.01); *G01R 31/2632* (2013.01)

(58) Field of Classification Search
CPC ............ G01R 1/06794; G01R 1/06716; G01R 1/06722; G01R 1/07378; G01R 1/2886; G01R 1/07314; G01R 1/07371; G01R 1/07342; G01R 31/26; G01R 31/2866; G01R 31/2831; G01R 31/2632; G01R 31/2648; G01R 31/2889; G01R 27/08; G01R 19/145; G01R 19/155
USPC .................. 324/754.01–754.03, 754.11, 149
See application file for complete search history.

(56) References Cited

U.S. PATENT DOCUMENTS

| | | | |
|---|---|---|---|
| 5,491,427 A | 2/1996 | Ueno et al. | |
| 5,663,657 A | 9/1997 | Lagowski et al. | |
| 6,368,887 B1 * | 4/2002 | Lowrey | H01L 22/20 438/14 |
| 6,972,582 B2 * | 12/2005 | Howland | G01R 31/2831 324/750.26 |
| 7,362,088 B1 | 4/2008 | Faifer et al. | |
| 7,679,381 B2 | 3/2010 | Ma | |
| 7,714,596 B2 | 5/2010 | Chen et al. | |
| 7,804,294 B1 * | 9/2010 | Faifer | G01R 31/2656 324/750.3 |
| 9,069,035 B2 | 6/2015 | Chen | |
| 2004/0155240 A1 * | 8/2004 | Howland | G01R 31/2831 257/48 |
| 2007/0170933 A1 * | 7/2007 | Ma | G01N 21/6489 324/754.03 |
| 2007/0170934 A1 | 7/2007 | Ma | |
| 2011/0298485 A1 * | 12/2011 | Narazaki | G01R 31/026 324/755.05 |
| 2012/0133388 A1 | 5/2012 | Bernoux et al. | |
| 2013/0043875 A1 | 2/2013 | Chen | |
| 2013/0046496 A1 * | 2/2013 | Chen | G01R 31/2648 702/65 |
| 2014/0303916 A1 * | 10/2014 | Mazzeo | G01R 27/14 702/65 |

OTHER PUBLICATIONS

Single Point Kelvin Probe System, KP020, KP Technology USA Inc., 2 pages, www.airphotoemission.com, www.kelvinprobe.com.
S.W. Lee et al., Origin of forward leakage current in GaN-based light-emitting devices, Appl. Phys. Lett., vol. 89, 132117, Sep. 28, 2016, 3 pages, American Institute of Physics.

* cited by examiner

APPARATUS AND METHOD FOR ACCURATE MEASUREMENT AND MAPPING OF FORWARD AND REVERSE-BIAS CURRENT-VOLTAGE CHARACTERISTICS OF LARGE AREA LATERAL P-N JUNCTIONS

CROSS-REFERENCE TO RELATED APPLICATIONS

The present application claims the benefit under 35 U.S.C. §119(e) of U.S. Provisional Application Ser. No. 61/873,545, filed Sep. 4, 2013. Said U.S. Provisional Application Ser. No. 61/873,545 is hereby incorporated by reference in its entirety.

TECHNICAL FIELD

The disclosure generally relates to measurement of current-voltage characteristics, and particularly to measurement of current-voltage characteristics of large area lateral p-n junctions as exist on a wafer immediately following active-layer formation during semiconductor manufacturing.

BACKGROUND

Thin polished plates such as silicon wafers and the like are a very important part of modern technology. A wafer, for instance, may refer to a thin slice of semiconductor material used in the fabrication of integrated circuits and other devices such as light emitting diodes, solar cells, or discrete diodes and transistors.

A p-n junction refers to a boundary or interface between two types of semiconductor material, p-type and n-type, inside a semiconductor. Advances in semiconductor technology have increased the requirements in measuring accuracy of the various characteristics of p-n junctions. Yield tracking and prediction requires reduced time to determine information of true electrical characteristics of devices being manufactured. Such characteristics may include current-voltage characteristics (I-V curves), sheet resistance and conductance measurements, leakage current measurements under reverse bias and forward voltage under forward bias, and the like. For instance, forward-voltage measured at 10 uA and 100 uA, as well as reverse current measured at −5V, are important manufacturing metrics for GaInN light-emitting diode (LED) manufacturers.

Currently, 4-point probe (4PP) techniques, such as the technique disclosed in U.S. Pat. No. 7,714,596, can be used for sheet resistance and conductance measurements by applying bias between top and bottom sides of wafers with p-n junctions. However, the existing 4PP techniques cannot be used for measurements of leakage current in GaInN LED structures on dielectric substrates such as sapphire. Another disadvantage of the existing 4PP techniques is that they are based on measurements of p-n junction conductance at very low reverse bias (<26 mV, also known as the linear regime where V<kT/q), which is not high enough for monitoring leakage current in GaInN LED structures in wide range of reverse bias (for example in the applied bias range 0 to −30V).

Other techniques for leakage measurements, such as those disclosed in U.S. Pat. App. No. 2013/0046496, U.S. Pat. App. No. 2013/0043875, and U.S. Pat. No. 7,679,381, use spring loaded probes to provide measurements of current-voltage characteristics (I-V curves). One of the main disadvantages of these techniques is related to the absence of any approach taking into account lateral current that strongly depends on the sheet resistance of p-n junction layers. This is critical because the lateral current leads to decreasing the current density, especially under reverse bias. Without knowing the current spreading, the current density is unknown. Other disadvantages of these techniques include severe measurement artifacts due to contact resistance as well as difficulties to contact the bottom layer of p-n junction grown on dielectric substrates such as sapphire.

Therein lies a need for systems and methods for accurate measurement and mapping of current-voltage characteristics under reverse as well as forward bias conditions of p-n junctions without the aforementioned shortcomings.

SUMMARY

The present disclosure is directed to an apparatus. The apparatus includes a first probe configured for establishing an electrical connection with a surface of a first layer of a p-n junction. The electrical connection established by the first probe covers an area of the surface of the first layer of the p-n junction optimized to minimize lateral current. The apparatus also includes a second probe configured for contacting the p-n junction and a measurement unit electrically connected to the first probe and the second probe. The measurement unit is configured for measuring at least one of: a voltage between the first and the second probes and a current between the first and the second probes when the first and the second probes are stimulated.

A further embodiment of the present disclosure is directed to an apparatus. The apparatus includes a first probe configured for establishing an electrical connection with a surface of a first layer of a p-n junction and a second probe configured for contacting the p-n junction. The apparatus also includes a plurality of voltage measurement probes configured for measuring a surface voltage drop and a guard loop configured for preventing lateral current from the first probe, wherein at least one of: a voltage and a current applied to the guard loop is adjustable based on the measured surface voltage drop. The apparatus further includes a measurement unit electrically connected to the first probe and the second probe, the measurement unit configured for measuring at least one of: a voltage between the first and the second probes and a current between the first and the second probes when the first and the second probes are stimulated.

An additional embodiment of the present disclosure is directed to an apparatus. The apparatus includes a first probe configured for establishing an electrical connection with a surface of a first layer of a p-n junction and a second probe configured for contacting the p-n junction. The apparatus also includes a plurality of voltage measurement probes configured for measuring surface voltages at different distances away from the first probe when the first and the second probes are stimulated. The apparatus further includes at least one additional probe configured for facilitating measurement of sheet resistance of the first layer of the p-n junction and a measurement unit configured for calculating a lateral current in proximity to the first probe based on the measured surface voltages at different distances away from the first probe and the measured sheet resistance.

An additional embodiment of the present disclosure is directed to a method. The method includes: stimulating a current between a first probe and a second probe connected to a p-n junction; measuring surface voltages at different distances away from the first probe when the first and the second probes are stimulated; measuring sheet resistance of a first layer of the p-n junction; and calculating a lateral current in proximity to the first probe based on the measured surface voltages at different distances away from the first probe and the measured sheet resistance.

An additional embodiment of the present disclosure is directed to a method. This includes: stimulating a current J between a first probe and a second probe connected to a p-n junction; measuring surface voltage $V_1$ using a first voltage measurement probe located a first distance away from the first probe, the first voltage measurement probe having a radius $R_{probe1}$; measuring surface voltage $V_2$ using a second voltage measurement probe located a second distance away from the first probe, the second voltage measurement probe having a radius $R_{probe2}$; and calculating sheet resistance of the p-n junction based on the current J, the surface voltage $V_1$, the surface voltage $V_2$, the radius $R_{probe1}$ and the radius $R_{probe2}$.

It is to be understood that both the foregoing general description and the following detailed description are exemplary and explanatory only and are not necessarily restrictive of the present disclosure. The accompanying drawings, which are incorporated in and constitute a part of the specification, illustrate subject matter of the disclosure. Together, the descriptions and the drawings serve to explain the principles of the disclosure.

BRIEF DESCRIPTION OF THE DRAWINGS

The numerous advantages of the disclosure may be better understood by those skilled in the art by reference to the accompanying figures in which.

DETAILED DESCRIPTION

Reference will now be made in detail to the subject matter disclosed, which is illustrated in the accompanying drawings.

Figure 1:
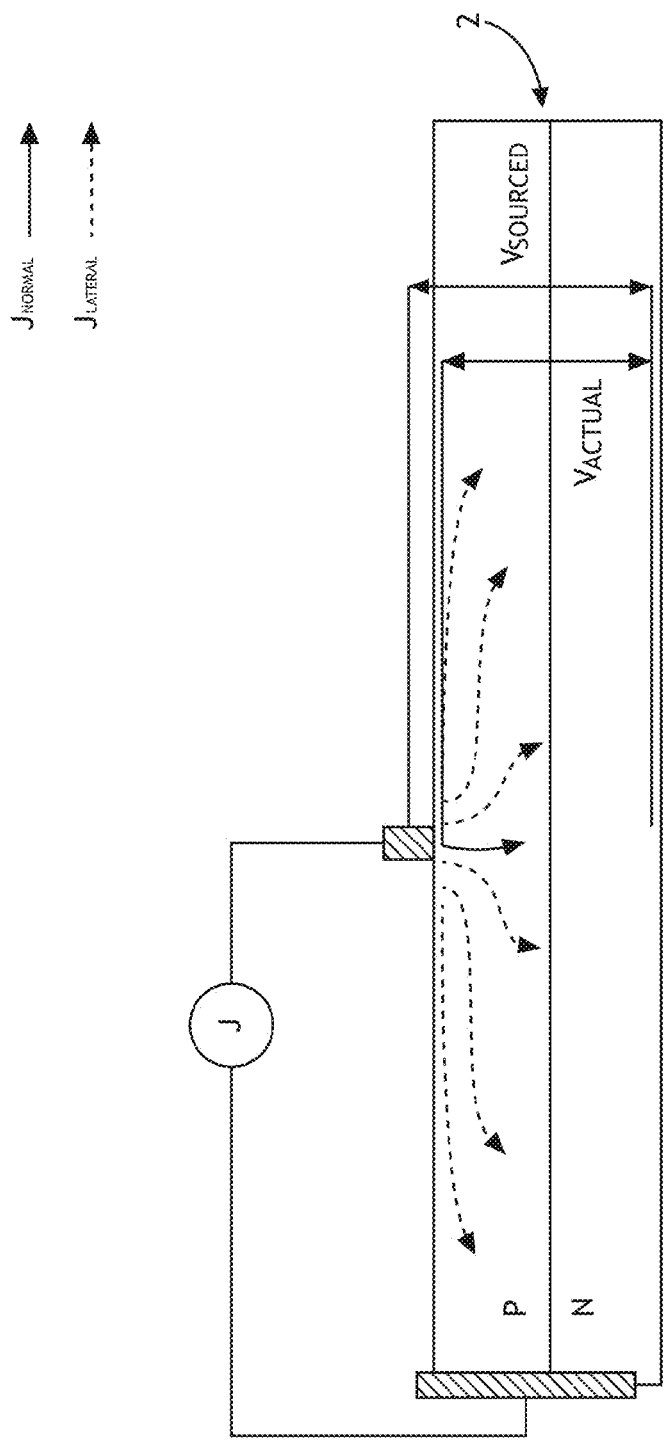
FIG. 1 is an illustration depicting lateral spreading of current in a p-n junction.

FIG. 1 is an illustration depicting the lateral movement (spreading) of current that may occur in a wafer 2 when measured using a typical measurement tool. More specifically, a typical measurement tool may provide a single contact to the wafer 2 to establish a connection to the p-layer and another contact to the wafer edge to establish a connection to the n-layer. The problem with this technique is that the majority of the current moves laterally through the p-layer ($J_{lateral} > J_{norm}$). It is noted that $J_{lateral}$ (i.e., the current referred to as lateral current) may flow normal to the surface (or through the junction) at some distance from the main normal current flow (i.e., $J_{norm}$). However, this distance is unknown, meaning that the density of current flowing through the junction at any given point is unknown. In addition, the current density (electrons/time/area) and the contact resistance between the contacting electrode and the wafer surface are unknown. These factors may all contribute to measurement inaccuracies.

The present disclosure is directed to methods and systems for providing measurements in p-n junctions and taking into account the lateral current for improved accuracy. In some embodiments, the lateral current may be controlled, allowing the spreading of the current to be reduced or substantially eliminated. In some other embodiments, the lateral current may be measured, allowing a more accurate normal current to be calculated by compensating for the measured spreading. In addition, the techniques utilized for controlling the lateral current and the techniques utilized for measuring the lateral current may also be implemented jointly.

Figure 2:
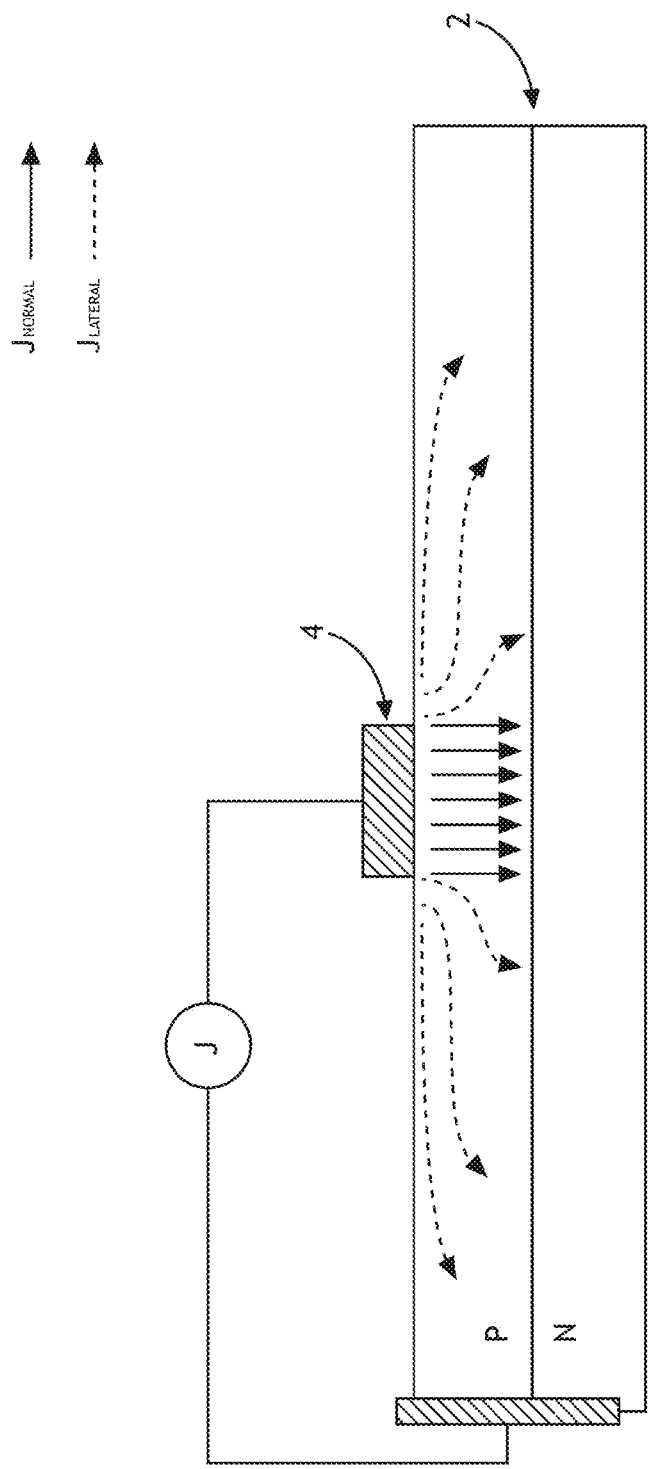
FIG. 2 is an illustration depicting a technique for controlling the lateral current in accordance with an embodiment of the present disclosure.

Referring now to FIG. 2, a technique for controlling the lateral current in accordance with an embodiment of the present disclosure is shown. More specifically, a primary current supply probe 4 may utilize a large area electrode for stimulating a current, J, through an area of p-n junction to provide the normal part of the current, $J_{norm}$. Utilizing a large area probe 4 allows $J_{norm}$ to be much higher than the lateral spreading of the current, $J_{lateral}$, where $J_{lateral} = J - J_{norm}$. Such conditions may be achieved by a disc type probe with its diameter optimized for specific sheet and shunt resistances to obtain $J_{norm} \gg J_{lateral}$. This optimization may be achieved by increasing the probe diameter and finding the optimal value when calculated density of leakage current (normalized to area) is minimized.

Figure 3:
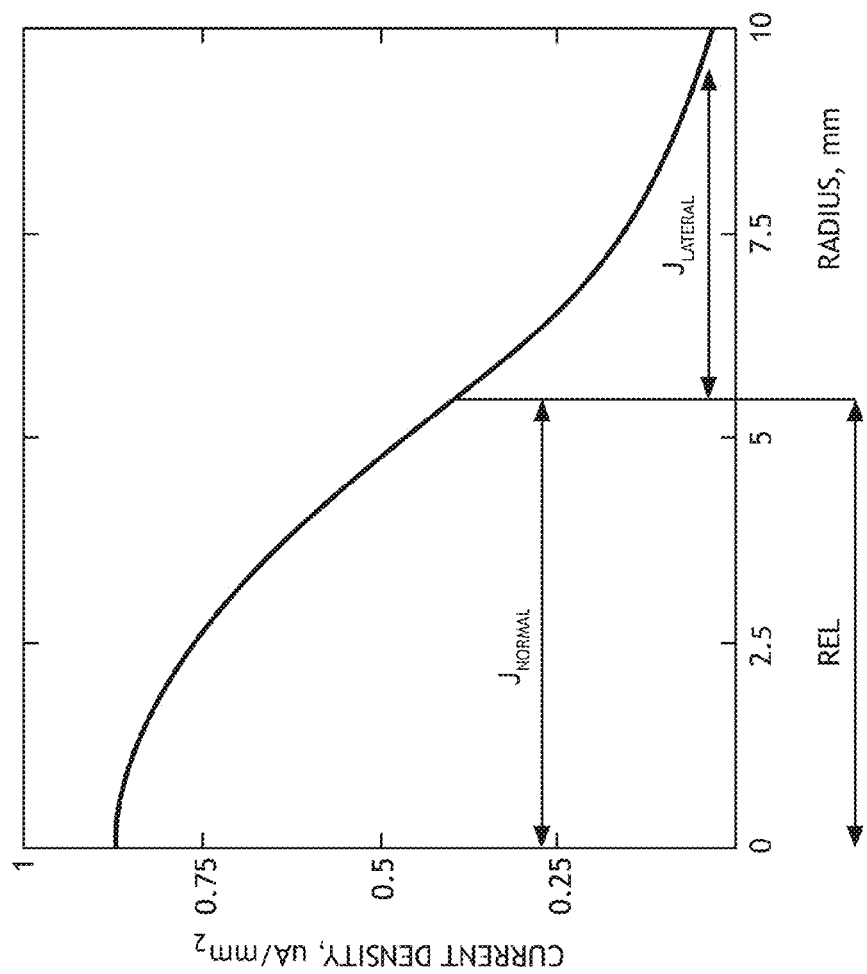
FIG. 3 is an illustration depicting the relationship between the distribution density of leakage current and the radius of the probe.

FIG. 3 is an illustration depicting the distribution density of leakage current 9 as a function of the radius of the probe with respect to leakage current $J_{norm}$ inside of the probe. It is noted that the apparent current density decreases as probe size increases. That is, the optimal probe diameter may be determined in order to diminish current flow $J_{lateral}$ outside of the probe. Mathematically, let the total leakage current through the p-n junction be denoted as $J = J_{norm} + J_{lateral}$, where $J_{norm}$ is the current inside and $J_{lateral}$ is the current outside of the contact area of the probe 4. It has been determined that ratio $$\frac{J_{norm}}{J_{lateral}}$$

increases as the contact area increases. Relating to the configurations shown in FIGS. 2 and 3, the radius $R_{EL}$ of the probe 4 may be configured to be large enough to provide conditions $J_{norm} \gg J_{lateral}$ and density of leakage current j under reverse bias voltage V (e.g., V=-5 V as for GaInN LED structures) can be determined using formula:

$$j \approx J/\pi R_{EL}^2$$

It is noted that according to experiments and simulations results, condition $J_{norm} \gg J_{lateral}$ can be achieved if $R_{EL} > 5$ mm in some embodiments. It is also noted that measurements may also be performed with probe 4 diameter equal to the diameter of the wafer 2 (lateral current=0). In this case, the average leakage current at applied reverse voltage (for example -5V) equals the measured current/wafer 2 area. However, it may not always be desirable or practical to set the probe 4 diameter equal to the diameter of the wafer 2, and in some implementations, the size of the probe 4 may be optimized to define a minimal size that provides maximum mapping capabilities and satisfies certain measurement accuracy requirements.

In some embodiments, to optimize the diameter of the probe 4 in order to provide the required measurement accuracy and spatial resolution, a set of electrodes with different diameters may be tested and an optimal diameter may be identified when density of leakage current calculated using the formula above reaches saturation within an error threshold. This condition may also be used for measurement of forward voltage $V_{flow}$ by applying low forward current (e.g., j=10 µA/mm2). It is to be understood, however, that the specific implementations and dimensions of the probe 4 may vary without departing from the spirit and scope of the present disclosure.

Figure 4:
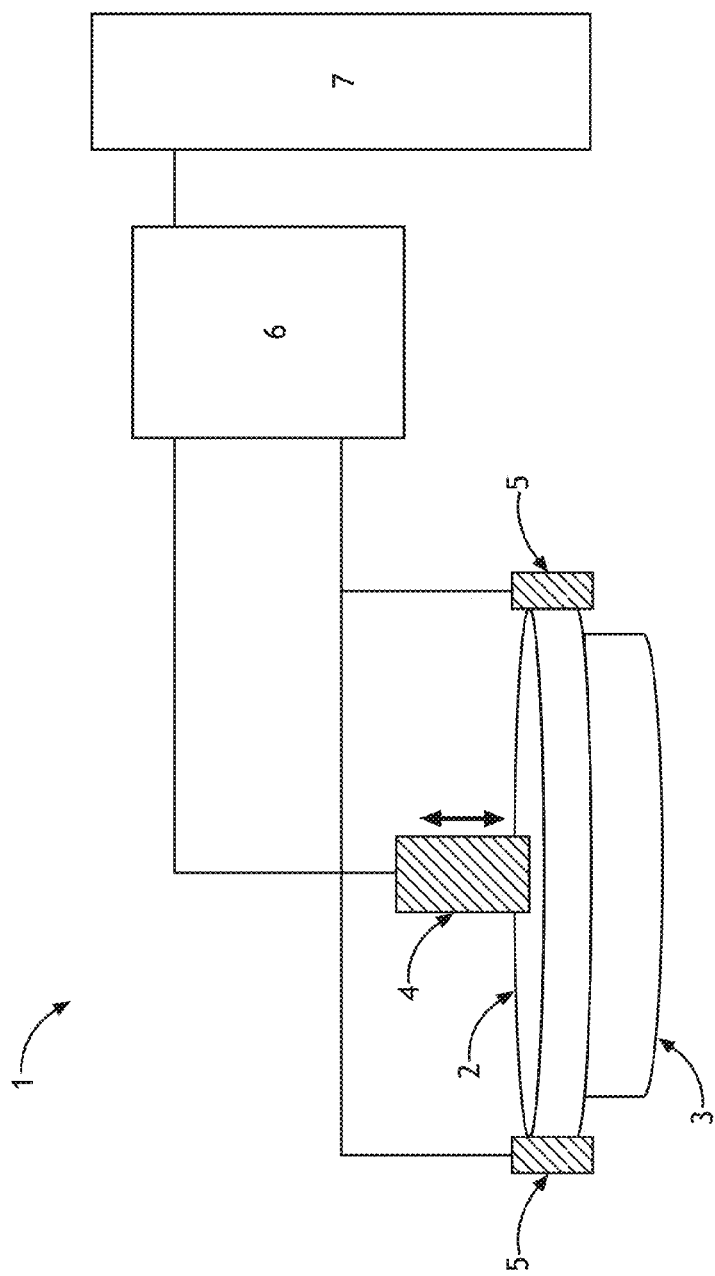
FIG. 4 is a block diagram depicting a measurement apparatus.
Figure 5:
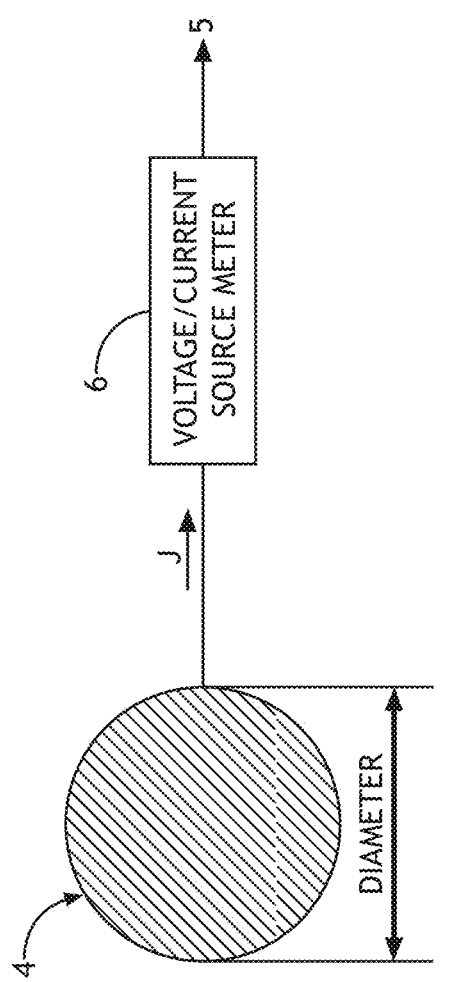
FIG. 5 is an illustration depicting a top view of a large area probe.
Figure 6:
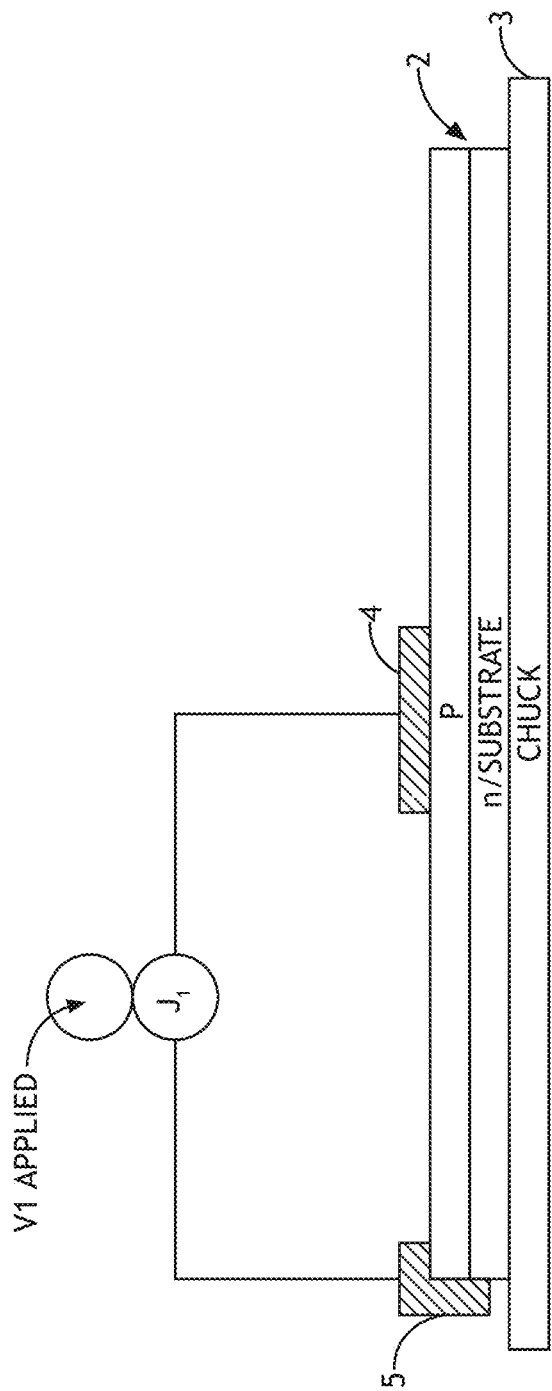
FIG. 6 is an illustration depicting voltage/current applied to the large area probe shown in FIG. 5.

FIGS. 4 through 6 are illustrations depicting an apparatus 1 that implements the technique illustrated in FIG. 2. As shown in FIG. 4, a wafer 2 containing a p-n junction is placed on a wafer chuck 3 of the apparatus 1. The apparatus 1 includes a probe 4 contacting the top surface of wafer 2 and one or more probes (electrodes) 5 contacting the bottom p-n junction layer. Both the probe 4 and the electrodes 5 are connected to a current/voltage source and measurement unit 6, forming an electrical path. The current/voltage source and measurement unit 6 may be electrically connected to a processor (e.g., a computer or a controller) 7.

As shown in FIGS. 5 and 6, the probe 4 may be implemented as a large area electrode to stimulate current $J_1$ between top contact and bottom contact using an applied voltage $v_{1,applied}$. The large area probe 4 may be implemented as a conductive elastic polymer (may also be referred to as conductive elastomer) electrode to be compliant to the wafer surface. The large area probe 4 may also be mounted to a mechanical actuator (e.g., gimbal-mounted) for even distribution of pressure and be in full compliance to angular offsets of the wafer surfaces. Alternatively/additionally, the large area probe 4 may also be mounted to a mechanical flexure that allows it to comply to the wafer surface while being rotationally fixed. It is contemplated that the specific implementation of the large area probe 4 may vary, as long as the area covered by the large area probe 4 is sufficiently large to diminish current flow outside of the large area probe 4 so that the normal part of the current $J_{norm}$ is much higher than the lateral spreading of the current $J_{lateral}$ as previously mentioned.

Figure 7:
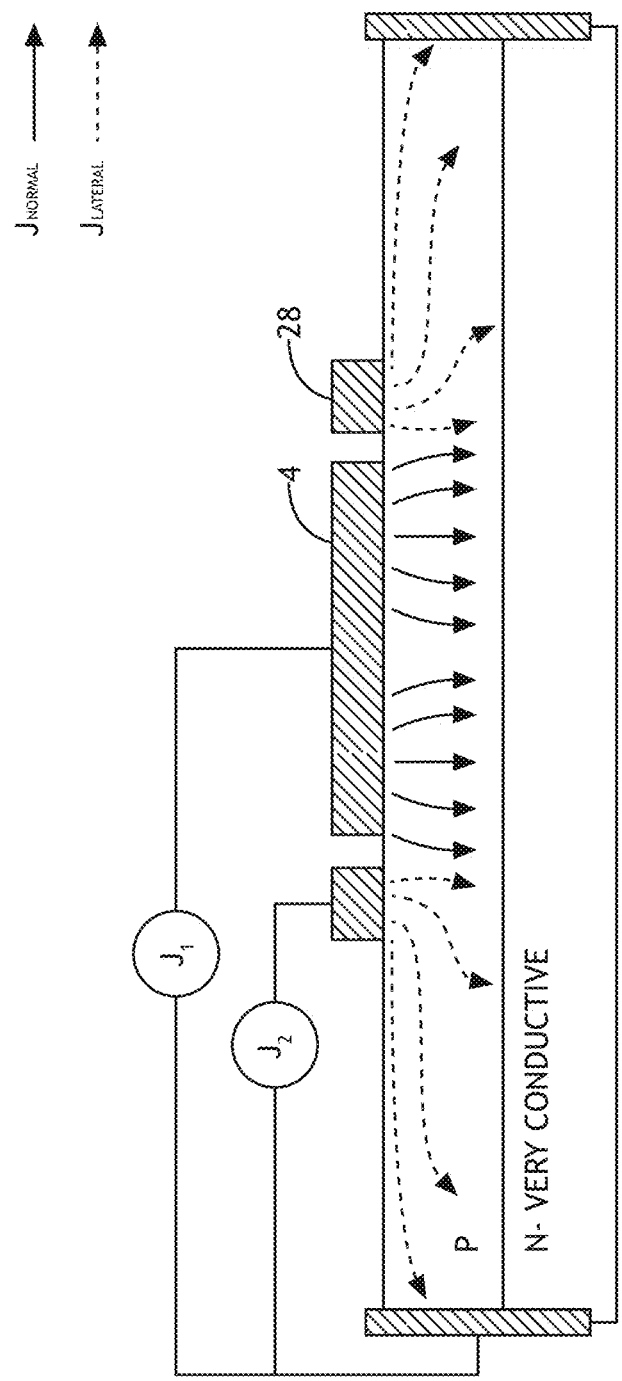
FIG. 7 is an illustration depicting a guard loop surrounding the large area probe.
Figure 8:
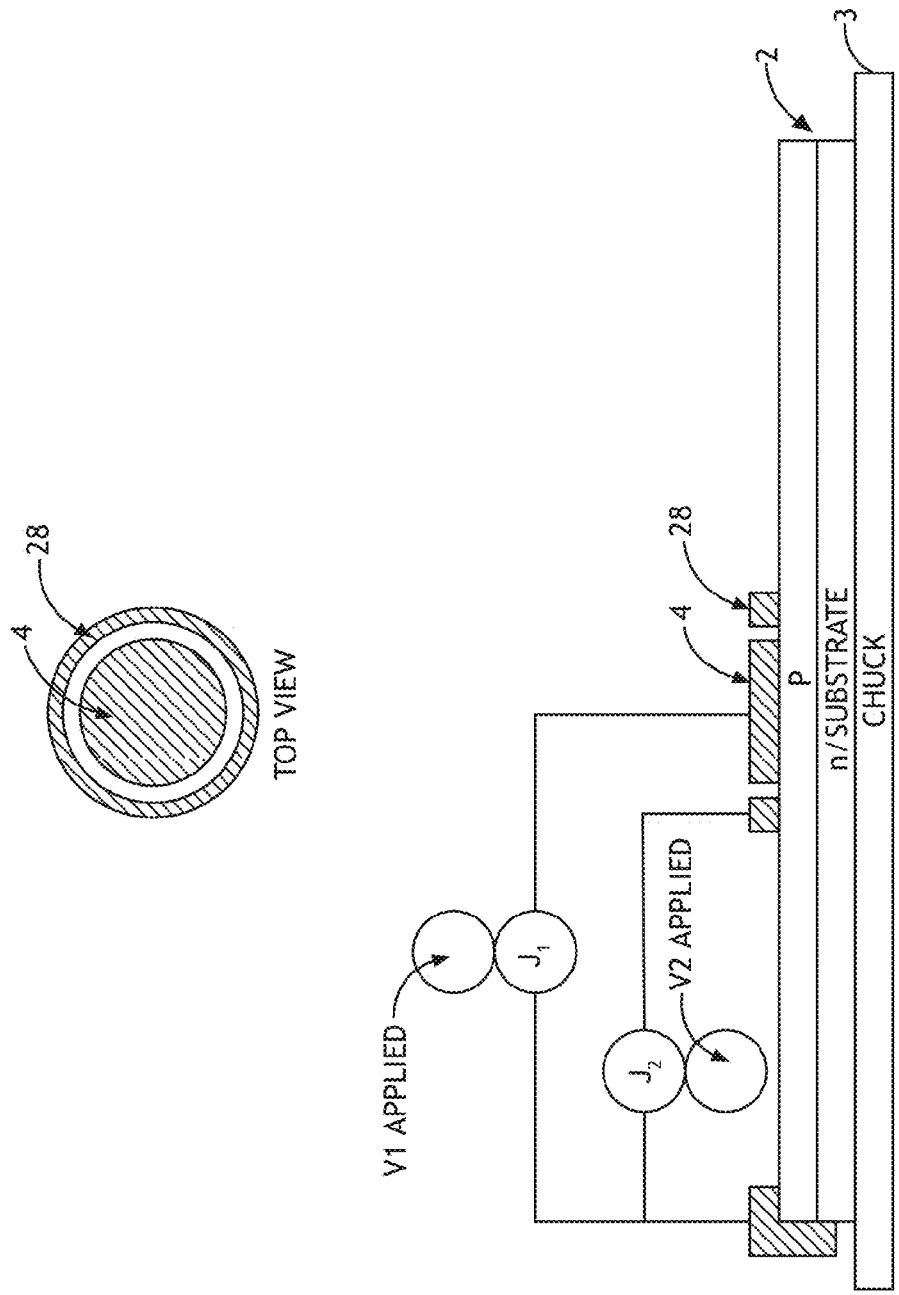
FIG. 8 is an illustration depicting voltage/current applied to the large area probe and the guard loop as shown in FIG. 7.

While using a large area probe 4 to obtain $J_{norm} \gg J_{lateral}$ effectively improves measurement accuracy, a further improvement may allow the spreading of the current to be substantially or completely eliminated. This technique is illustrated in FIGS. 7 and 8. More specifically, in addition to utilizing the primary probe 4 to stimulate the current, an exterior guard electrode 28 (depicted as an exterior guard ring in FIGS. 7 and 8) electrically connected to a second current source may be utilized to help prevent lateral current spreading from the primary probe 4 (may be referred to as the main electrode). By providing a similar voltage on the guard electrode 28 as on the primary electrode 4, the lateral electrical field and therefore the lateral current $J_{lateral}$ can be significantly reduced. In addition, it is contemplated that surface voltages may be measured at certain wafer surface locations (the details of which will be described later), and the current provided by the second source to the guard electrode 28 may be adjusted accordingly to equalize the measured voltages, allowing the lateral electrical field and therefore the lateral current $J_{lateral}$ to be eliminated completely.

Figure 9:
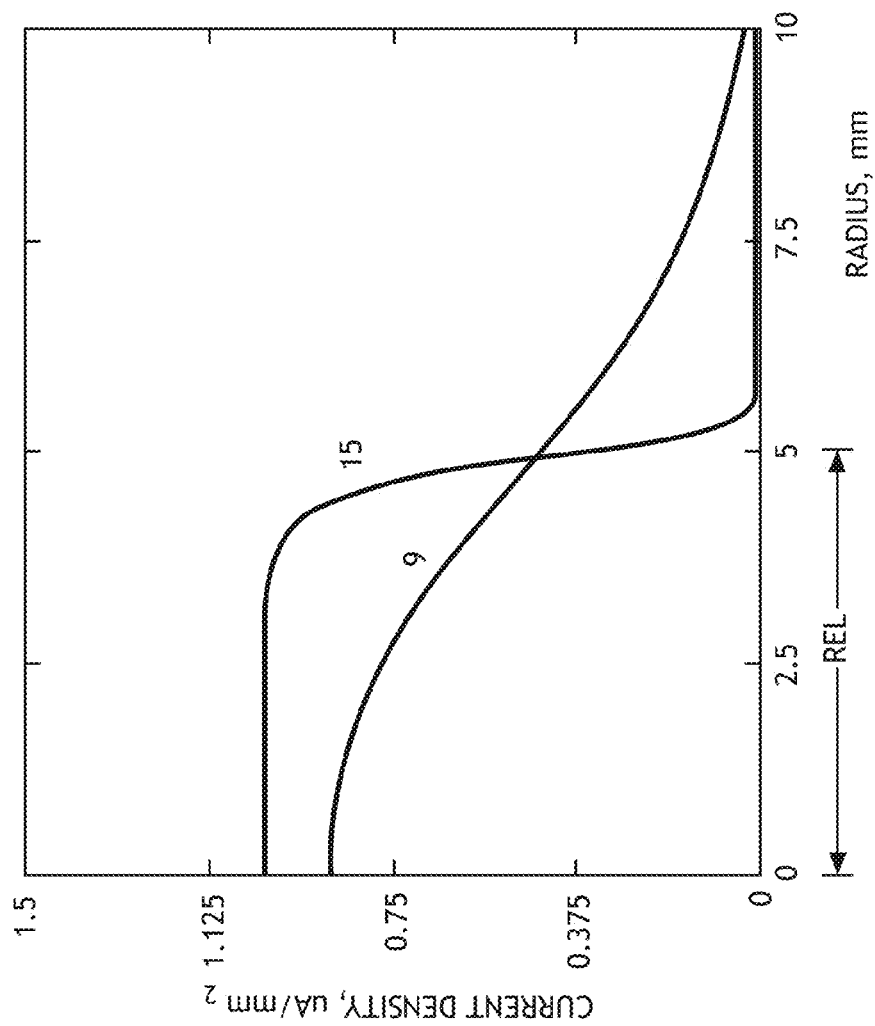
FIG. 9 is an illustration depicting the relationship between the distribution density of leakage current and the radius of the probe with the implementation of the guard loop.

The effectiveness of using the guard electrode 28 is depicted in an exemplary simulation result shown in FIG. 9. It is noted that applying voltage to the guard electrode 28 leads to decrease of lateral current promoting uniform leakage current localized within the contact area of the primary electrode 4 (illustrated using curve 15). It is also noted that using the guard electrode 28 may effectively relax the condition that $J_{norm} \gg J_{lateral}$ since the ratio $$\frac{J_{norm}}{J_{lateral}}$$

may no longer be a concern. Therefore, using the guard electrode 28 may allow a smaller electrode to be utilized as the primary electrode 4, providing a higher spatial resolution which may be appreciated especially when available surface spaces are limited.

It is to be understood that the techniques for controlling the lateral current as described above, i.e., 1) using a large area probe and/or 2) using a guard electrode, may be implemented independently or jointly to control the lateral current without departing from the spirit and scope of the present disclosure. It is also to be understood that the generally disk- and ring-shaped electrodes described above are merely exemplary. It is contemplated that the primary electrode 4 may be configured to be oval-shaped, rectangular-shaped, polygon-shaped, or configured to have various other geometrical shapes. Similarly, it is contemplated that the guard electrode 28 may form any connected loop (not necessarily a ring-shaped loop), as long as the guard electrode 28 is capable of localizing the leakage current within the contact area of the electrode which the guard electrode 28 is configured to guard (e.g., primary electrode 4 in the examples presented above). It is contemplated that a guard electrode 28 configured in this manner may be generally referred to as a guard loop. The guard loop may also be formed using many contact pins spaced close-enough together to provide minimal voltage decay between the pins on the wafer surface.

It is also contemplated that the primary electrode 4 and the guard electrode 28 described above not only provide the abilities to control (reduce or eliminate) the lateral current, but may also provide the abilities to take more accurate measurements of various current and/or voltage characteristics of interest. For instance, the primary electrode 4 and the guard electrode 28 may be used jointly to stimulate the wafer surface and obtain the current-voltage characteristics (I-V curve) of the p-n junction.

Figure 10:
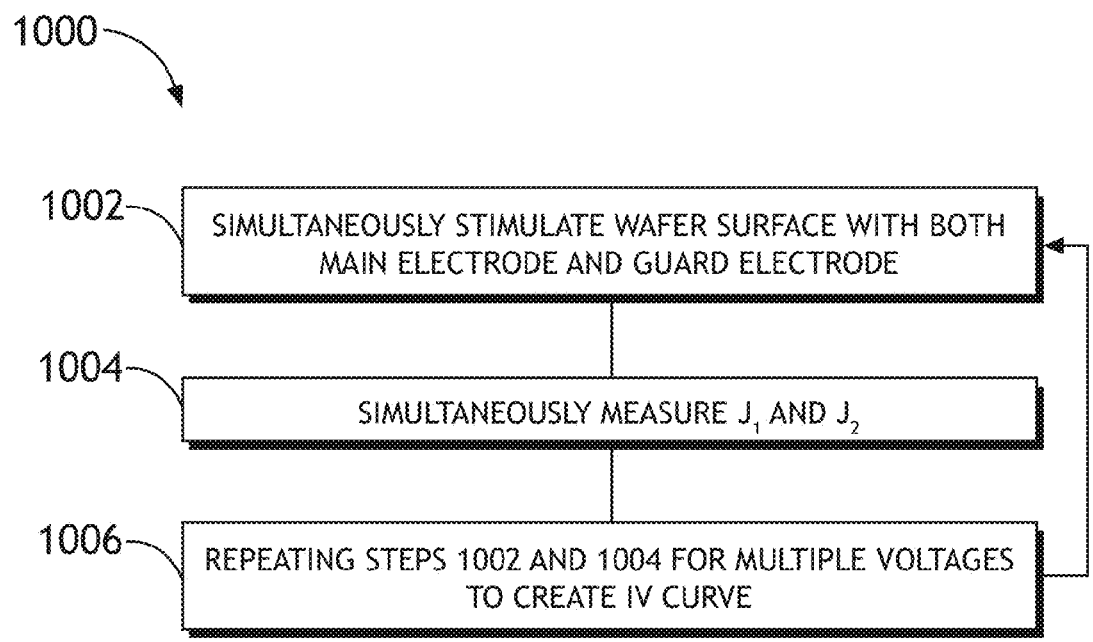
FIG. 10 is a flow diagram depicting a method for obtaining I-V curve of the p-n junction.

As shown in FIG. 10, a method 1000 may be utilized to obtain the I-V curve of the p-n junction. More specifically, in step 1002, both the primary electrode 4 and the guard electrode 28 held at potentials $v_{1,applied}$ and $v_{2,applied}$, where $v_{1,applied} = v_{2,applied}$, may be used to simultaneously stimulate the wafer surface. The corresponding current, $J_1$ and $J_2$, may be measured in step 1004. This process may be repeated for a plurality of different voltages to obtain the I-V curve under forward as well as reverse bias conditions in step 1006.

Figure 11:
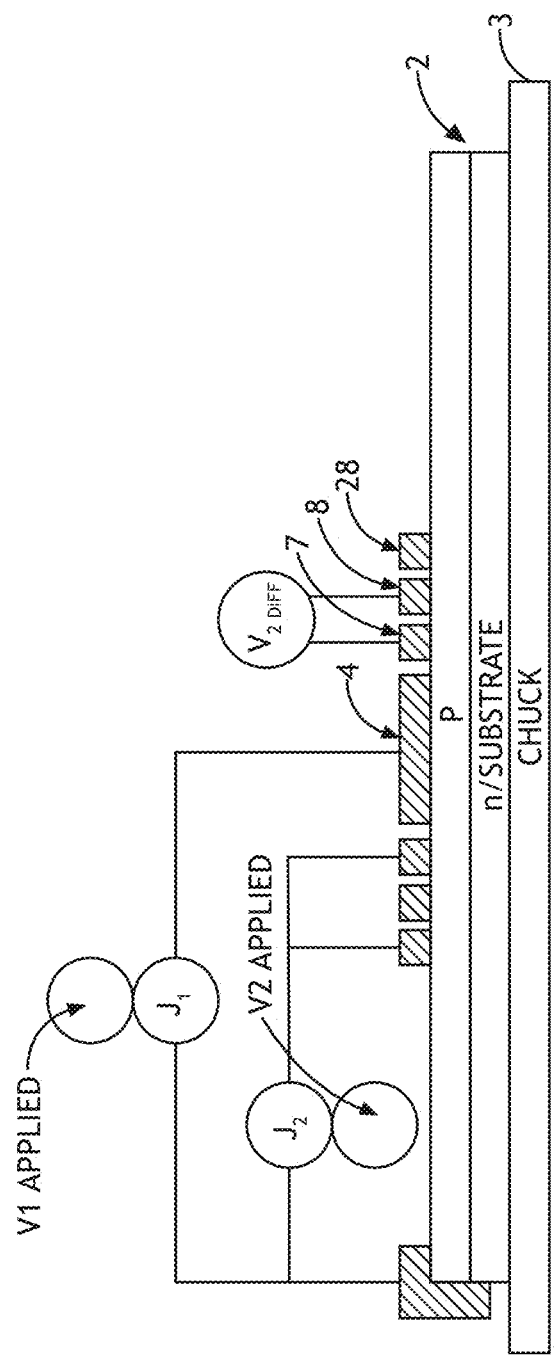
FIG. 11 is an illustration depicting measurement of surface voltage differential.

It is noted that the measured current $J_1$ should be representative of normal current flowing through the junction and the measured current $J_2$ should include the lateral current. However, due to differences in contact resistance between the two electrodes 4 and 28, there may be a small voltage differential on the surface allowing small lateral currents to flow from the primary electrode 4, which may negatively impact the accuracy of the I-V curve obtained. To take into account this small voltage differential on the surface, two or more electrical contacts 7 and 8 may be established in the space between the primary electrode 4 and the guard electrode 28, as illustrated in FIG. 11, to measure the surface voltage differential $v_{2,diff}$ in the region between the primary electrode 4 and the guard electrode 28.

Figure 12:
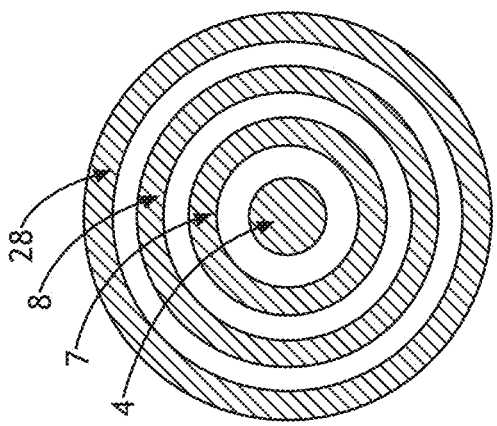
FIG. 12 is a top view of voltage measurement probes positioned between a primary probe and a guard loop.
Figure 13:
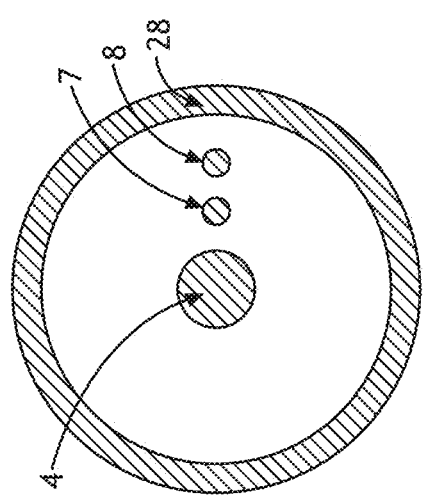
FIG. 13 is a top view of different types of voltage measurement probes positioned between a primary probe and a guard loop.

It is to be understood that the electrical contacts 7 and 8 may be established utilizing various types of electrodes. For instance, as shown in FIG. 12, two ring electrodes 7 and 8 may be utilized to establish electrical connections with the wafer surface. Alternatively, as shown in FIG. 13, the electrical contacts 7 and 8 may be established using small disc electrodes without forming the rings depicted in FIG. 12. It is to be understood that the electrical contacts 7 and 8 may be established in various manners without departing from the spirit and scope of the present disclosure.

Figure 14:
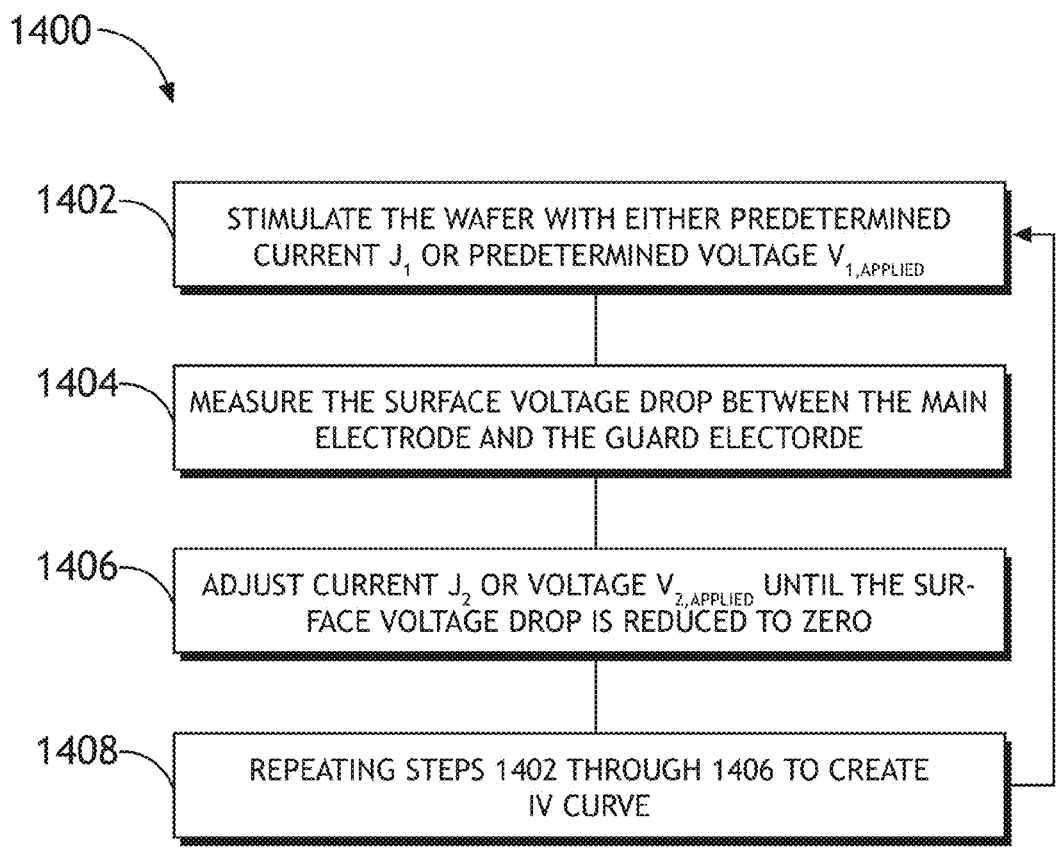
FIG. 14 is a flow diagram depicting a method for obtaining I-V curve of the p-n junction, taking into account the surface voltage differential.

FIG. 14 shows a method 1400 for obtaining the I-V curve of the p-n junction while taking into account the surface voltage differential $v_{2,diff}$ between the primary electrode 4 and the guard electrode 28. More specifically, in step 1402, either a predetermined voltage $v_{1,applied}$ or a predetermined current $J_1$ may be utilized to stimulate the junction at the primary electrode 4. The surface voltage drop between the primary electrode 4 and the guard electrode 28 may be measured in step 1404 based on the surface voltage differential $v_{2,diff}$ at contacts 7 and 8. Subsequently, in step 1406, voltage $v_{2,applied}$ (or current $J_2$) applied to the guard electrode 28 may be adjusted until $v_{2,diff}$ reaches zero. By eliminating the lateral voltage differential, the lateral current is quenched. It is contemplated that the adjustment step 1406 may be performed using a feedback control loop (e.g., a high impedance differential amplifier with negative feedback). Once $v_{2,diff}$ reaches zero, the corresponding currents, $J_1$ and $J_2$, can be measured, and this process may be repeated for a plurality of different voltages $v_{1,applied}$ to obtain the I-V curve in step 1408.

Figure 15:
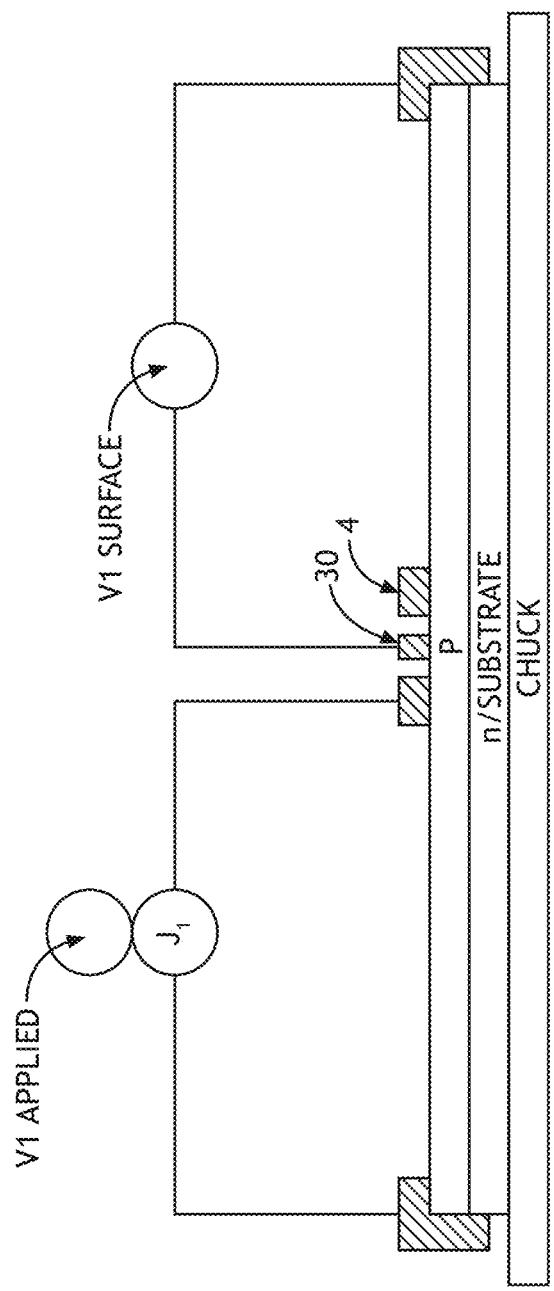
FIG. 15 is a voltage measurement probe located within the primary probe.
Figure 16:
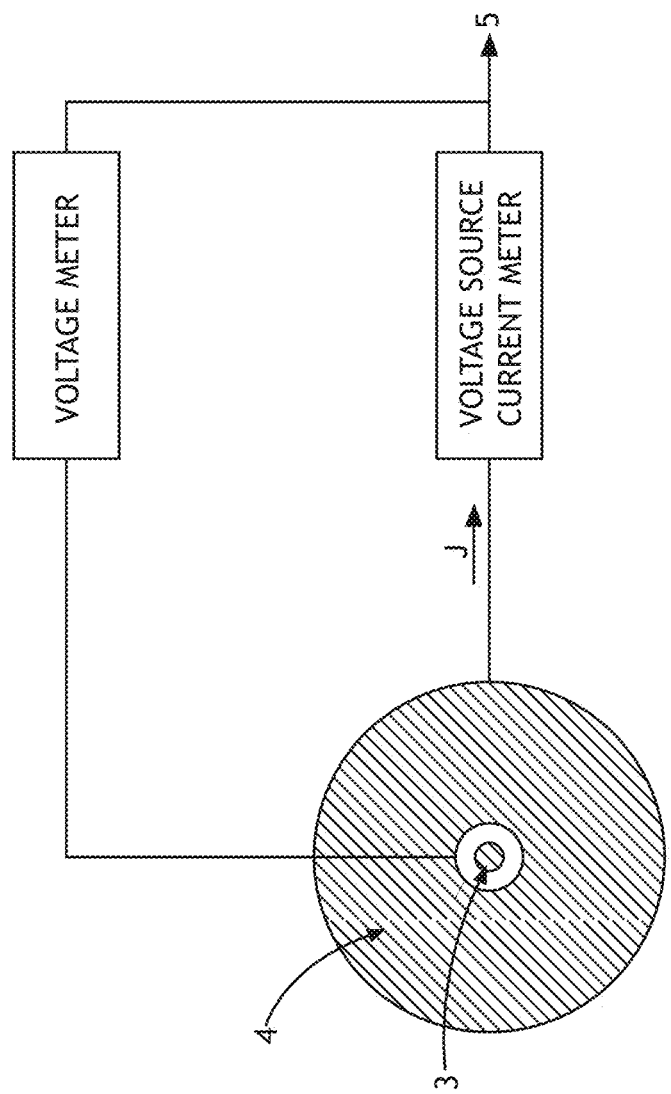
FIG. 16 is an illustration depicting a top view of the voltage measurement probe and the primary probe.

In addition to providing the abilities to obtain I-V curves, the probes 4, 28 and electrical contacts 7, 8, in accordance with embodiments of the present disclosure, may also be configured to support various other types of measurements for the p-n junction. FIGS. 15 and 16 are illustrations of an exemplary probe configuration that supports measurement of the actual potential on the surface of the wafer 2, $v_{1,surface}$ (i.e., the surface voltage).

More specifically, it is noted that the large area probe 4 is not required to form a solid disc-shaped contact with the wafer surface. In other words, an opening may be defined within the large area probe 4 while still maintaining a sufficiently large contact area with the wafer surface to stimulate current $J_1$ between top contact and bottom contact using an applied voltage $v_{1,applied}$. The opening defined within the large area probe 4 may therefore allow a pad 30 (e.g., another electrical contact independent from the probe 4) to establish a connection with the wafer surface. This pad 30 may be connected to a voltage meter (e.g., a high-impedance voltage meter), which may be used to measure the actual surface voltage $v_{1,surface}$. For instance, the measurement of $v_{1,surface}$ may be taken between the pad 30 and the bottom contact (e.g., contact 5) established on the n-layer of the wafer 2, or between the pad 30 and a different but similar contact to the n-layer of the wafer 2 to eliminate the inaccuracies due to any voltage drop due to contact resistance.

It is noted that placing the pad 30 within the probe 4 for measurement of the actual surface voltage $v_{1,surface}$ may be advantageous because it has been shown by both simulations and measurement results that the voltage measured inside the probe 4 has minimal lateral decay compared to measurements taken from the edge or outside of the probe 4. This lateral decay may be lower for reverse bias than for forward bias. For example, to provide accurate measurements in GaInN LED wafers of forward voltage under density of forward current of about 10 µA/mm2, the diameter of the pad 30 must be less than 2 mm. Furthermore, under forward bias conditions, the lateral decay also increases as the current is increased. In order to monitor the lateral decay, it is contemplated that two or more electrodes may be utilized and located within the opening defined by the probe 4 to monitor the lateral differential on the surface. This lateral differential may be used as an indicator to determine when the measured surface voltage $v_{1,surface}$ is no longer accurate.

It is also noted that having the ability to measure the actual surface voltage $v_{1,surface}$ provides several advantages. For instance, knowing the actual surface voltage allows the contact resistance between the contacting electrode and the wafer surface to be calculated based on formula $$\frac{v_{1,applied} - v_{1,surface}}{J_1}.$$

In addition, knowing the actual surface voltage also provides some alternative methods for obtaining the I-V curve in addition to the methods described above. For instance, some exemplary methods 1700 and 1800 for determining I-V curves are shown in FIGS. 17 and 18.

Figure 17:
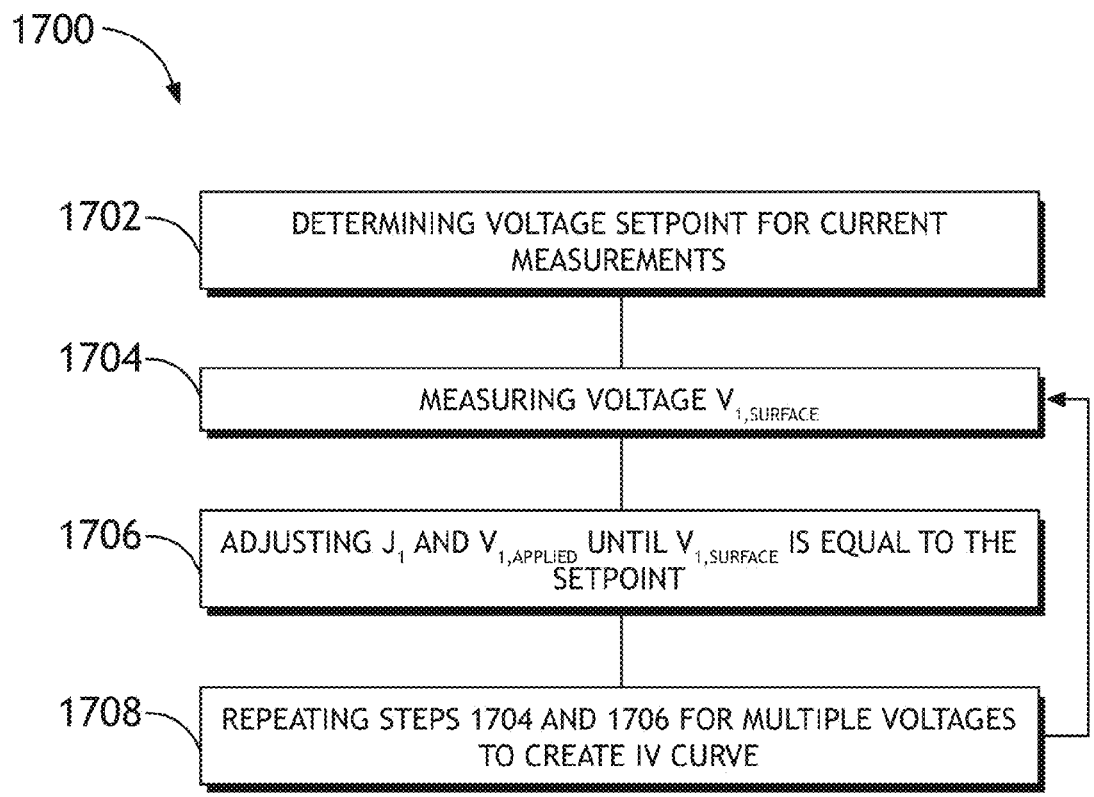
FIG. 17 is a flow diagram depicting a method for obtaining I-V curve of the p-n junction, taking into account the surface voltage measured within the primary probe.
Figure 18:
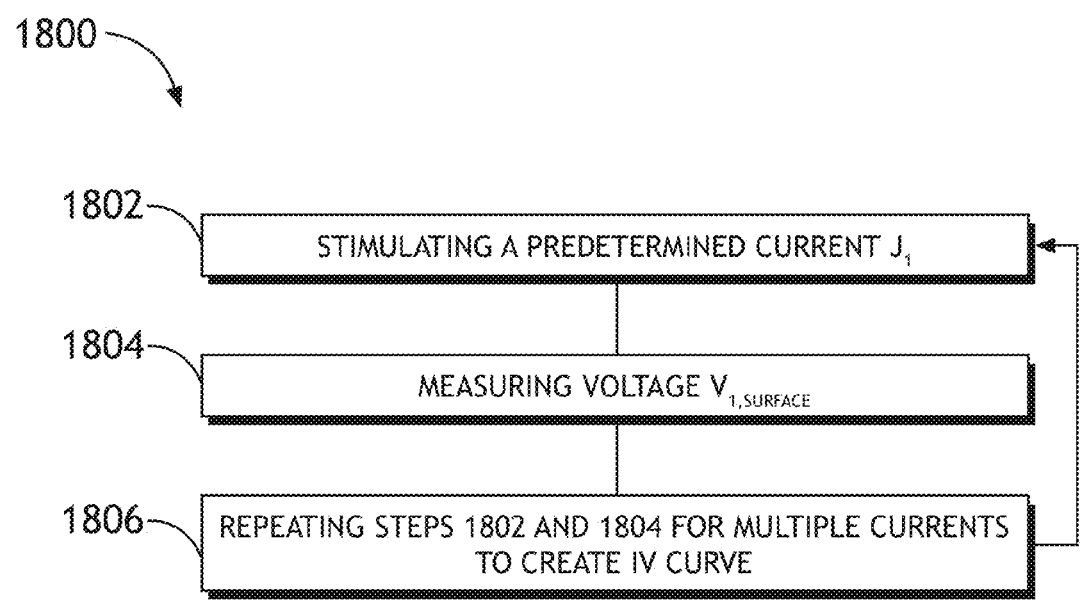
FIG. 18 is a flow diagram depicting another method for obtaining I-V curve of the p-n junction, taking into account the surface voltage measured within the primary probe.

As shown in FIG. 17, a voltage setpoint for current measurements may be established in step 1702. Step 1704 may measure the actual surface voltage $v_{1,surface}$ and step 1706 may adjust the current $J_1$ and the applied voltage $v_{1,applied}$ until $v_{1,surface}$ is equal to the setpoint. It is contemplated that step 1706 may be performed utilizing a feedback control loop. Subsequently, steps 1704 and 1706 may be repeated for a plurality of different voltages to obtain the I-V curve in step 1708. Alternatively, as shown in FIG. 18, a predetermined current $J_1$ may be utilized to stimulate the wafer 2 in step 1802. Step 1804 may measure the actual surface voltage $v_{1,surface}$ and this process may be repeated for a plurality of different predetermined currents to obtain the I-V curve in step 1806.

It is to be understood that the formulas and the methods for calculating contact resistance and/or the I-V curve as described above are merely exemplary. It is contemplated that the measured surface voltage $v_{1,surface}$ may be utilized for various other purposes in addition to calculations of contact resistance and/or the I-V curve without departing from the spirit and scope of the present disclosure.

Figure 19:
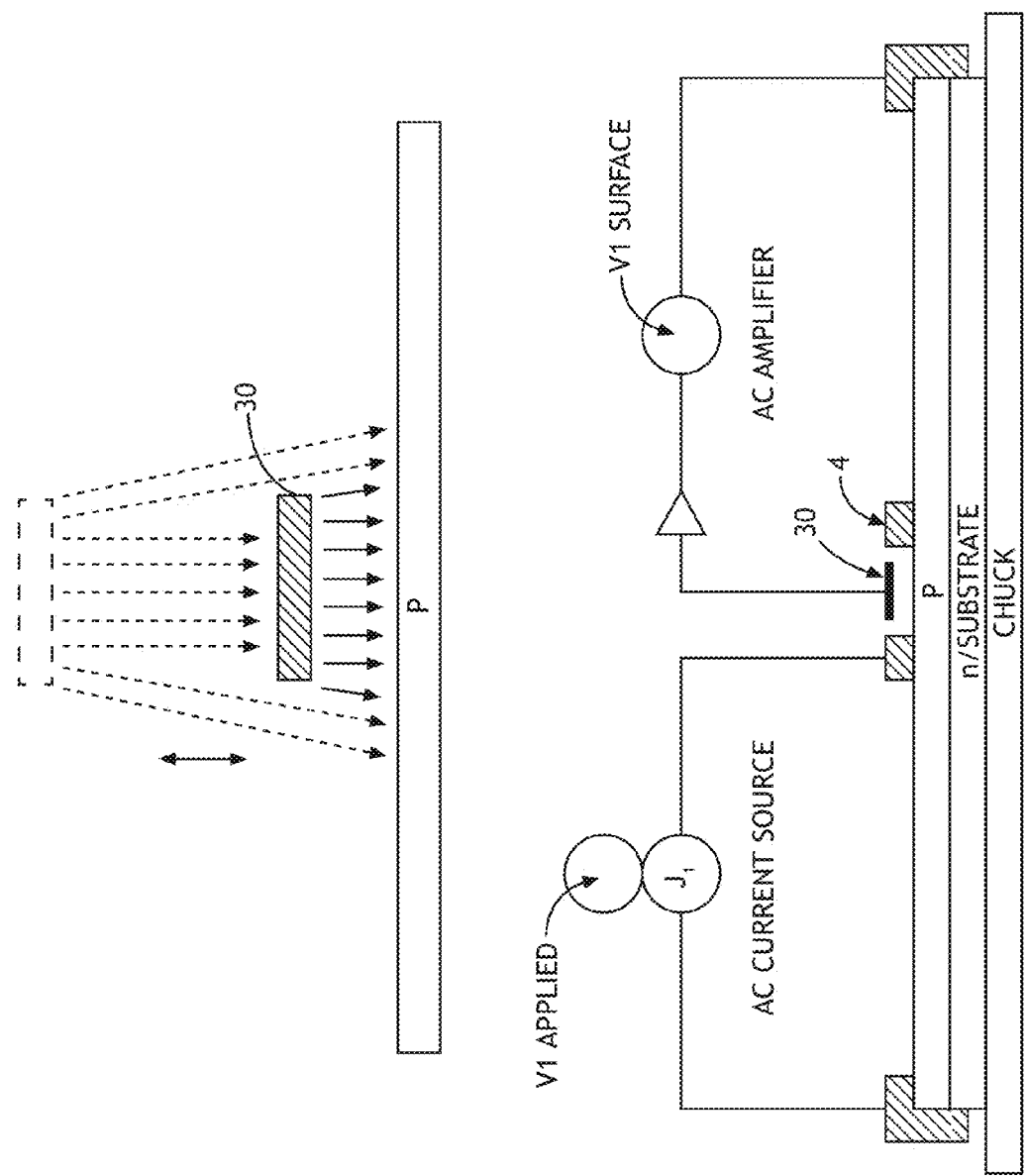
FIG. 19 is an illustration depicting a non-contact voltage measurement probe located within the primary probe.

It is also contemplated that the measurement of the surface voltage $v_{1,surface}$ may be accomplished without requiring a physical contact to be established between the pad 30 and the wafer surface. For instance, the pad 30 may be implemented as a non-contact pad 30 as depicted in FIG. 19. It is noted that various non-contact measurement techniques, such as those disclosed in U.S. patent application Ser. No. 14/475,025 entitled "METHOD AND APPARATUS FOR NON-CONTACT MEASUREMENT OF FORWARD VOLTAGE, SATURATION CURRENT DENSITY, IDEALITY FACTOR AND I-V CURVES IN P-N JUNCTIONS" (the disclosure of which is incorporated herein by reference), may be utilized to provide the measurement without departing from the spirit and scope of the present disclosure. Additionally/alternatively, the non-contact pad 30 may also be configured as a Kelvin probe and measurement of $v_{1,surface}$ may be done under DC current source. Kelvin probe may be small in diameter (e.g., <2 mm) and may decrease systematic errors of measurement especially under forward bias conditions. Furthermore, it is contemplated that the non-contact pad 30 may be configured to vary its distance from the surface, thereby changing the effective area of the non-contact pad 30 detection due to variation in the location of the fringing electric fields. By changing the effective area, the voltage distribution within the opening of probe 4 may be characterized.

Figure 20:
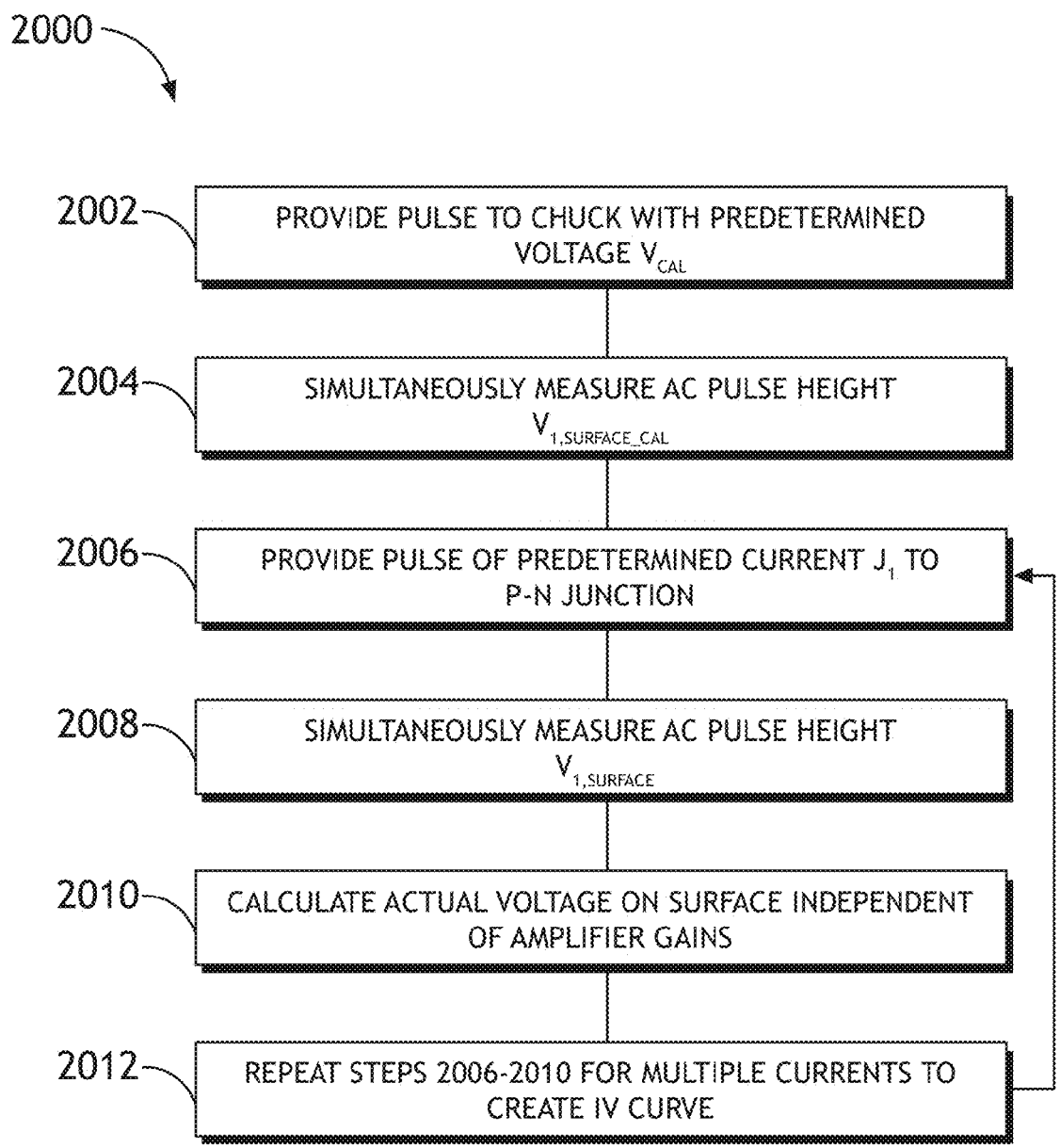
FIG. 20 is a flow diagram depicting a method for obtaining I-V curve of the p-n junction, wherein the current source is an AC source.

In addition, as depicted in FIG. 19, the current source utilized for the measurement of surface voltage is not limited to a direct current (DC) source; an alternating current (AC) source may also be utilized for the measurement of the surface voltage $v_{1,surface}$ without departing from the spirit and scope of the present disclosure. For instance, a method 2000 illustrated in FIG. 20 may be utilized to obtain the current-voltage characteristics of the wafer when an AC source is used.

More specifically, a pulse may be provided to chuck with a predetermined voltage $v_{cal}$ in step 2002 and the AC pulse height $v_{1,surface\_cal}$ may be measured substantially simultaneously in step 2004. In step 2006, a pulse of a predetermined current $J_1$ may be provided to the p-n junction, and the AC pulse height $v_{1,surface}$ may be measured substantially simultaneously in step 2008. The actual voltage on the wafer surface, $v_{actual}$, independent of any amplifier gains, may then be calculated in step 2010 as $$v_{actual} = \frac{v_{cal}}{v_{1_{surface\_cal}}} \times v_{1,surface}.$$

Steps 2006 through 2010 may then be repeated for a plurality of different predetermined currents to obtain the I-V curve in step 2012.

Figure 21:
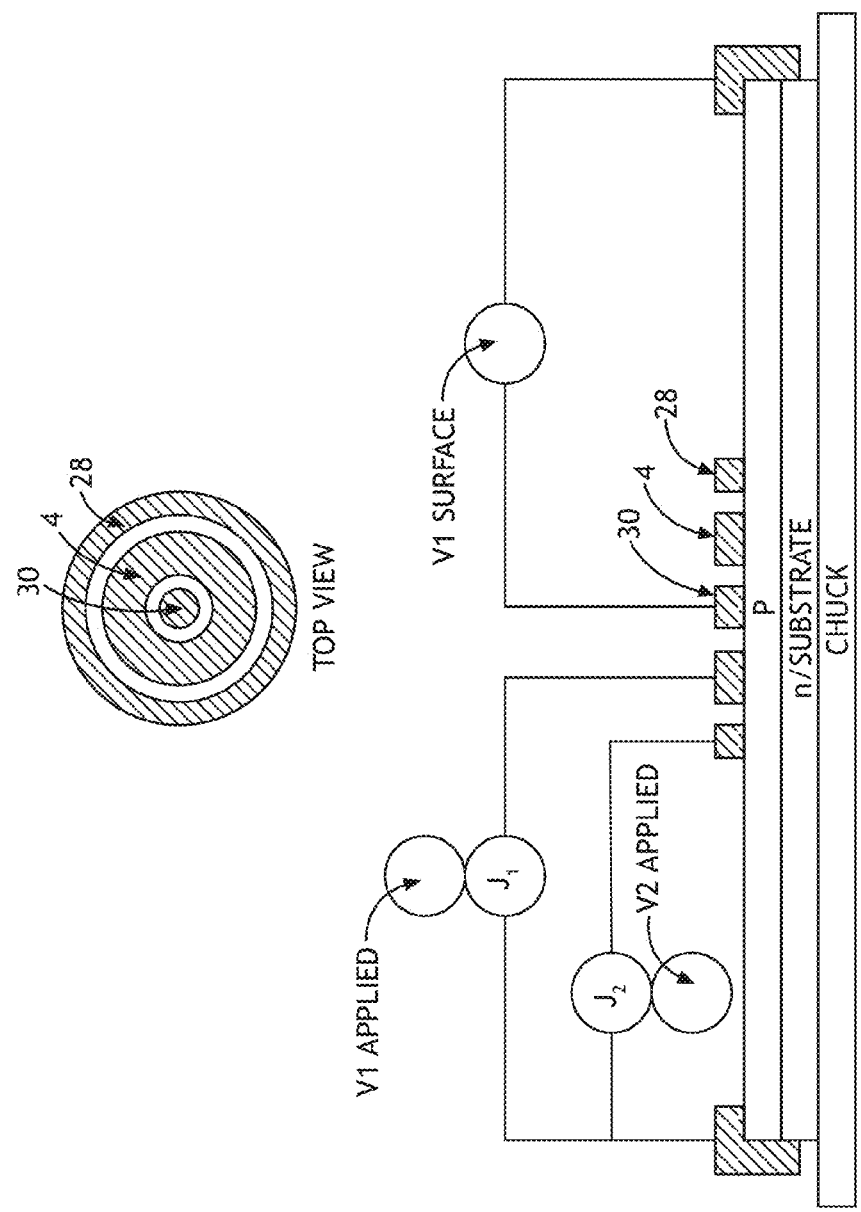
FIG. 21 is an illustration depicting a combination of a voltage measurement probe located within the primary probe and a guard loop.
Figure 22:
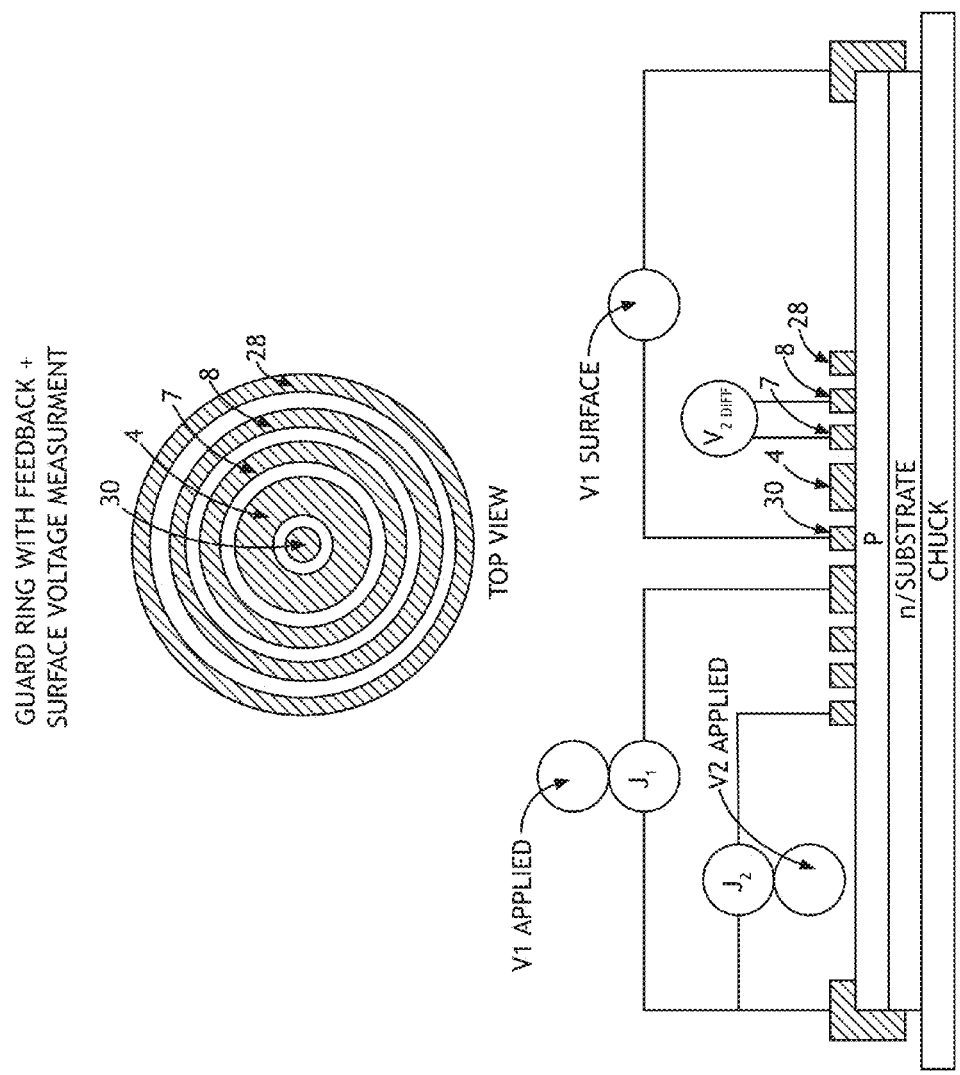
FIG. 22 is an illustration depicting a combination of a voltage measurement probe located within the primary probe, a guard loop, and a plurality of voltage measurement probes positioned between the primary probe and the guard loop.

It is noted that the pad 30 may also be utilized in conjunction with the guard electrode 28, as illustrated in FIG. 21. Additionally, two or more electrical contacts (e.g., contacts 7 and 8) may also be established in the space between the primary electrode 4 and the guard electrode 28 to measure the surface voltage differential $v_{2,diff}$ as illustrated in FIG. 22. It is contemplated that the various measurement methods previously described are still applicable.

Figure 23:
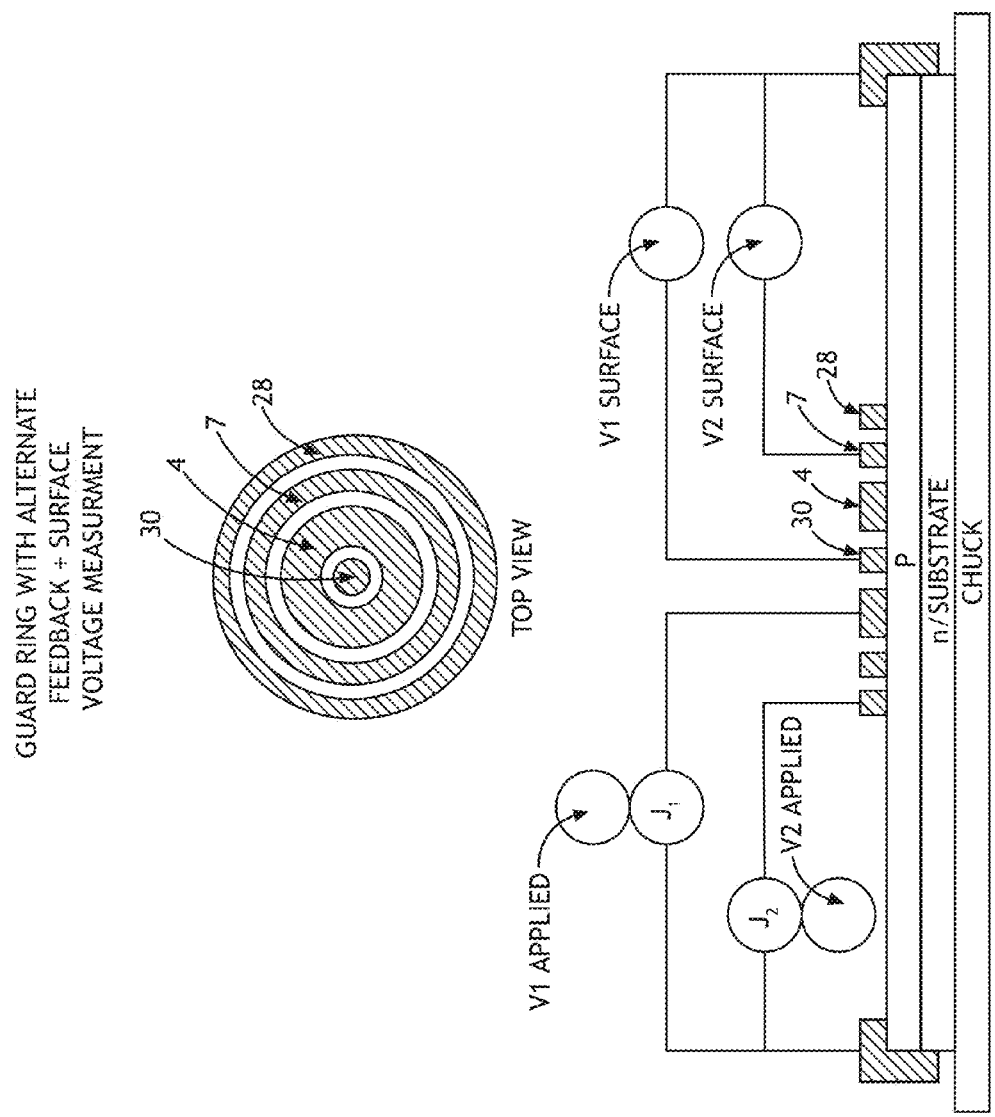
FIG. 23 is an illustration depicting a combination of a voltage measurement probe located within the primary probe, a guard loop, and one additional voltage measurement probe positioned between the primary probe and the guard loop.

It is further noted that since the pad 30 already provides the ability to measure the surface voltage at one location, it is not necessary to have two additional contacts 7 and 8 for the purpose of measuring the surface voltage differential. In some embodiments as shown in FIG. 23, only one additional contact (labeled 7 in this example) is needed to measure the surface voltage at a location different from the location of the pad 30. The two measured surface voltages, $v_{1,surface}$ and $v_{2,surface}$, may be utilized to adjust the current $J_2$ in order to eliminate the lateral voltage differential, similar to the eliminating process described in FIG. 14.

Figure 24:
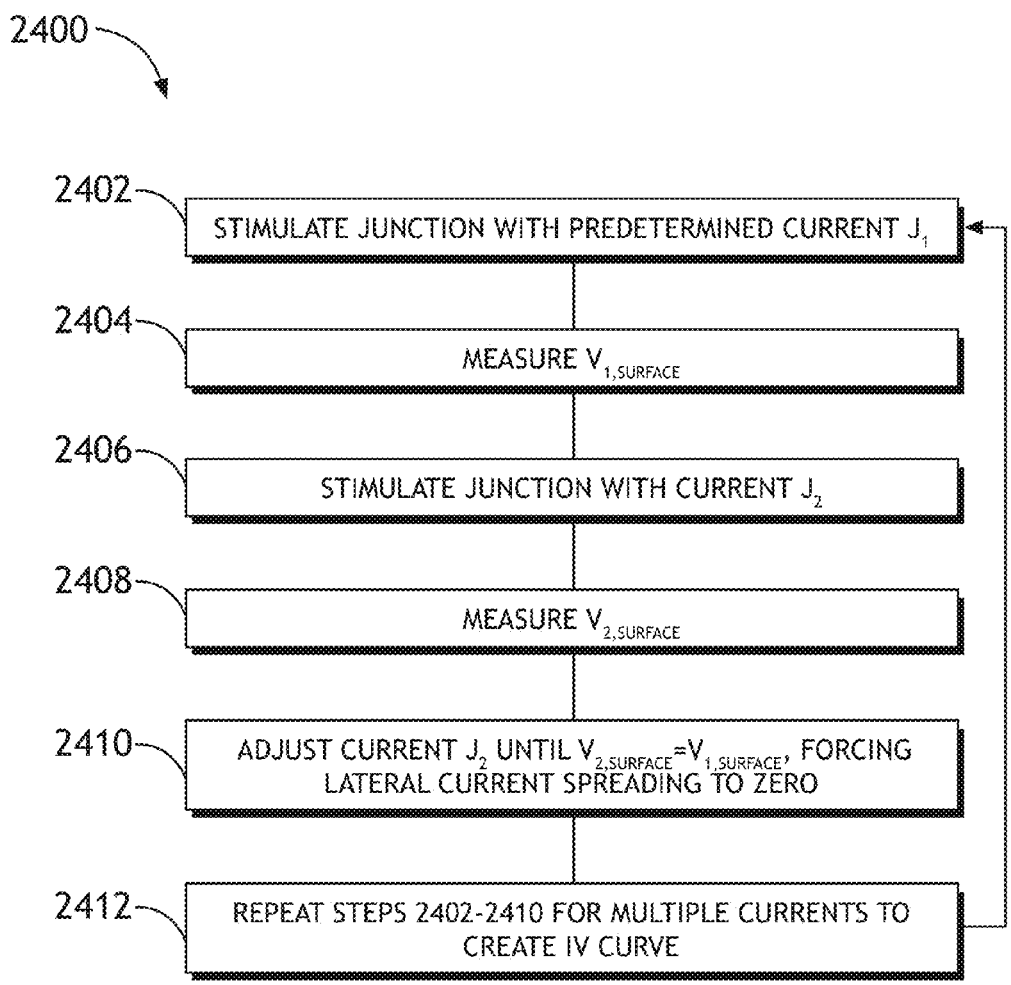
FIG. 24 is a flow diagram depicting a method for obtaining I-V curve of the p-n junction, wherein the lateral current is eliminated.

FIG. 24 shows a method 2400 for obtaining the I-V curve of the p-n junction while taking into account the two measured surface voltages, $v_{1,surface}$ and $v_{2,surface}$. More specifically, in step 2402, a predetermined current $J_1$ may be utilized to stimulate the junction at the primary electrode 4. The surface voltage $v_{1,surface}$ may then be measured in step 2404 using the pad 30. Optionally, if a voltage setpoint has been established, the current $J_1$ may be adjusted until $v_{1,surface}$ is equal to the setpoint. Step 2406 may stimulate the junction at the guard electrode 28 with current $J_2$ and the surface voltage $v_{2,surface}$ may be measured in step 2408. Subsequently, in step 2410, current $J_2$ may be adjusted until $v_{1,surface}$ equals $v_{1,surface}$, effectively forcing the lateral current spreading to zero. It is contemplated that the adjustment step 2410 may be performed using a feedback control loop, and once $v_{2,surface}$ equals $v_{1,surface}$, the corresponding current $J_1$ and $v_{1,surface}$ can be recorded and this process may be repeated for a plurality of different currents $J_1$ under forward as well as reverse bias conditions to obtain the I-V curve in step 2412.

To reiterate, it is noted that the various configurations of the probes (electrical contacts) described above provide various measurement abilities that include the measurement of the actual surface voltage $v_{1,surface}$ the contact resistance between the contacting electrode and the wafer surface, as well as the abilities to obtain I-V curves. It is contemplated that certain electrode configurations in accordance with embodiments of the present disclosure may further support the measurement of the p-layer sheet resistance $R_{sp}$.

For instance, in the various embodiments described above where probes 4, 7, 8 and 28 are present, these probes can be utilized to facilitate the determination of sheet resistance $R_{sp}$. More specifically, current J may be applied between probes 4 and 28 and the voltage V may be measured between probes 7 and 8. The sheet resistance $R_{sp}$ may then be calculated as:

$$R_{SP} = 2\pi \frac{V}{J} \ln\left(\frac{R_8}{R_7}\right)$$

Where $R_7$ and $R_8$ represent the radiuses of probes 7 and 8, respectively.

It is noted that knowing the sheet resistance also helps measuring the lateral current that may occur. This may allow a more accurate normal current to be calculated by compensating for the measured lateral current.

To effectively measure the lateral current, two or more electrical contacts may be placed outside of the current supply electrode, allowing the lateral voltage drop on the surface of the wafer 2 to be measured. The two or more electrical contacts may be configured in similar manners as the electrical contacts 7 and 8 previously described. That is, the two or more electrical contacts 7 and 8 placed outside of the current supply electrode (e.g., the primary electrode 4 in the examples above) may be configured as ring-shaped electrodes, small disc electrodes, or various other types of electrodes without departing from the spirit and scope of the present disclosure.

Figure 25:
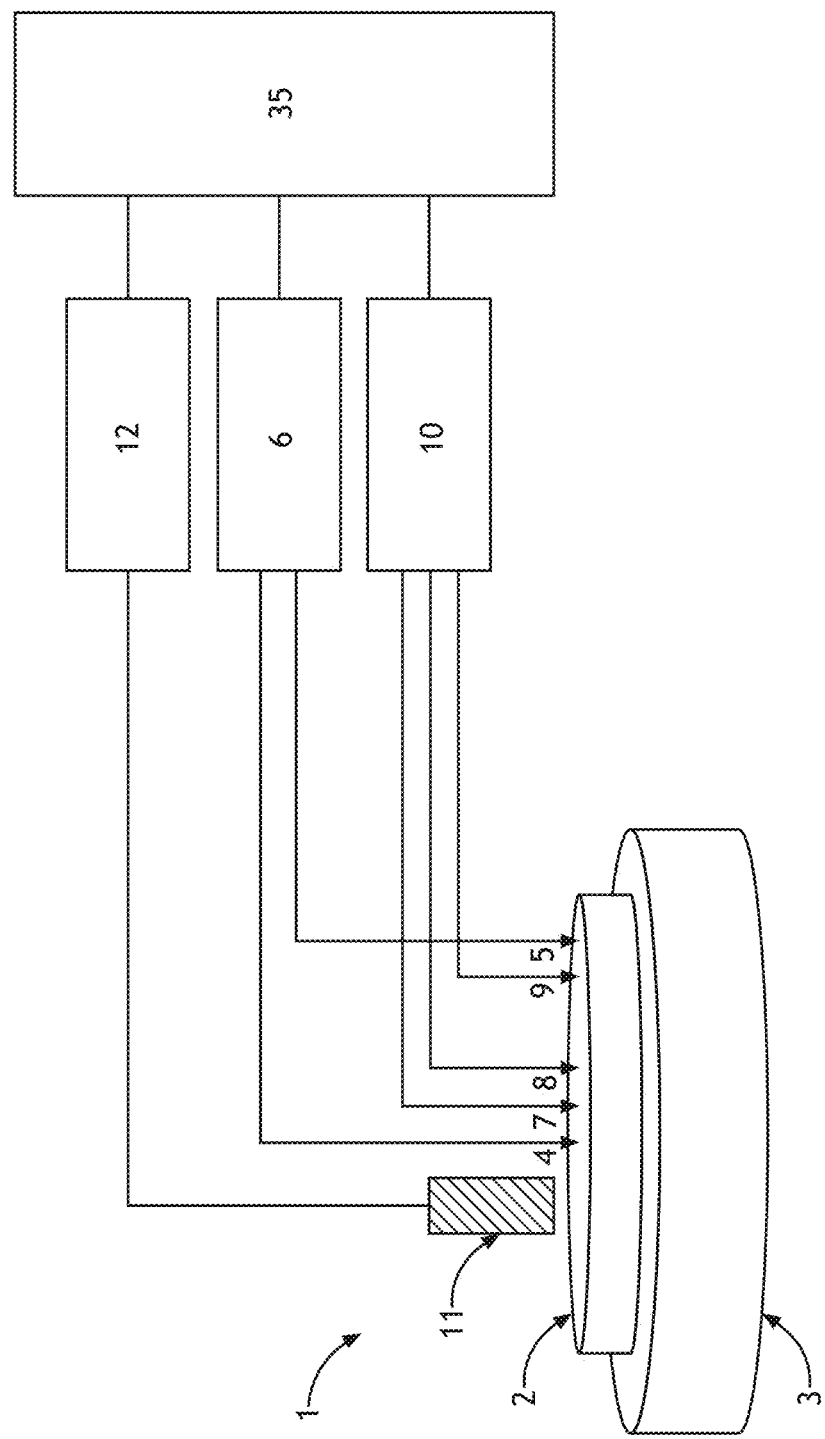
FIG. 25 is a block diagram depicting a measurement apparatus capable of measuring the lateral current.

Referring now to FIG. 25, a block diagram depicting the apparatus 1 capable of measuring the lateral current spreading from the current supply electrode 4 is shown. As previously described, the current supply electrode 4 may be implemented as a large area electrode optimized to obtain $J_{norm} \gg J_{lateral}$. However, such an implementation is not required.

As shown in FIG. 25, the wafer 2 containing a p-n junction is placed on a wafer chuck 3. Electrodes (probes) 4 and 5 are utilized to establish connections to the top surface of the wafer 2 and a current source 6. The apparatus 1 may also include electrodes (probes) 7, 8, and 9 connected to the top surface of the wafer 2 and a voltage meter 10. A sheet resistance measurement probe 11 may also be utilized to provide measurement of sheet resistance near electrode 4. The sheet resistance measurement probe 11 may be electrically connected to a sheet resistance probe control unit 12.

It is contemplated that the sheet resistance measurement probe 11 may be implemented as a four point probe (4PP) or a non-contact junction photovoltage probe, as disclosed in U.S. Provisional Pat. Appl. No. 61/718,138 (the disclosures of which is incorporated herein by reference) and especially designed for measurements of sheet resistance of top p-layer in GaInN LED structures.

The apparatus 1 may further include a computer (a processor) 35. The current source 6, the voltage meter 10, and the sheet resistance probe control unit 12 may be communicatively connected to the computer 35. The probes 4, 5, 7, 8, and 9 may be spring loaded probes such as pogo pins, modified four-point probe units, or may be comprised of compliant radiused tips, flat tips, large area conformal conductive elastomer tips, or the like.

Figure 26:
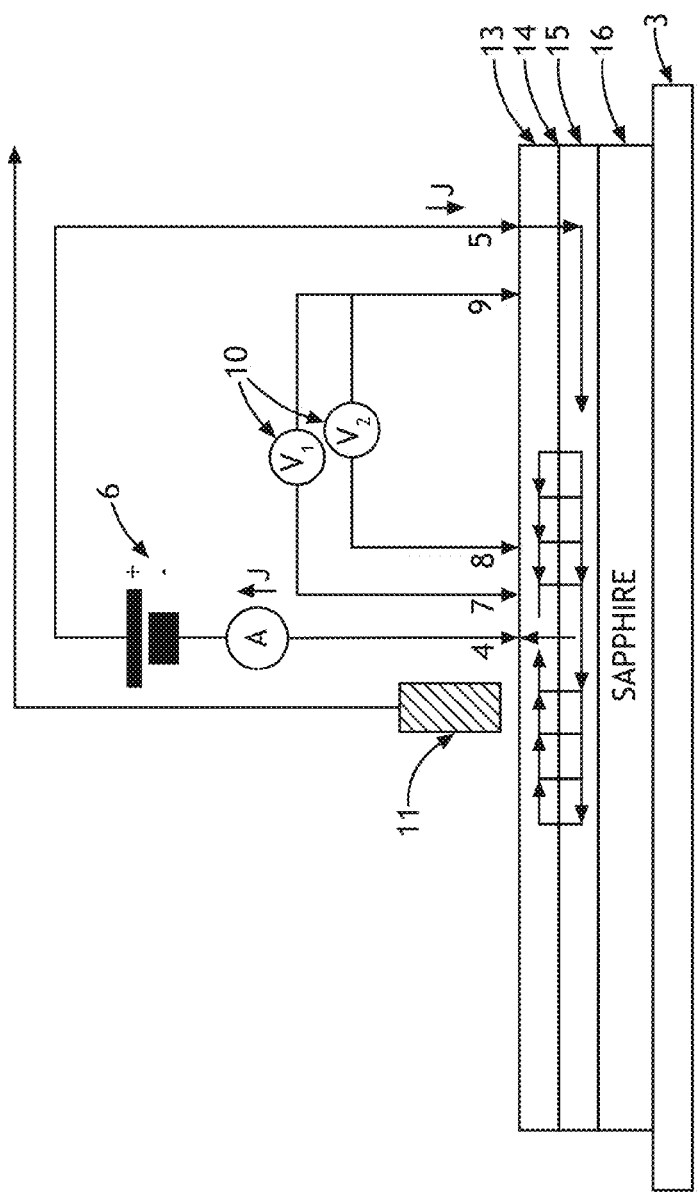
FIG. 26 is an illustration depicting current flow through the p-n junction and the leakage current under reverse bias.

For illustrative purposes, FIG. 26 shows the current flow through the p-n junction and the leakage current under reverse bias. More specifically, the p-layer 13, the n-layer 15, and the p-n junction layer 14 may be positioned on a sapphire substrate 16. Current J may flow from probe 5 to probe 4 through p-layer 13, p-n junction layer 14, and n-layer 15. A simplified equivalent circuit of the current flow is shown in FIG. 27.

Figure 27:
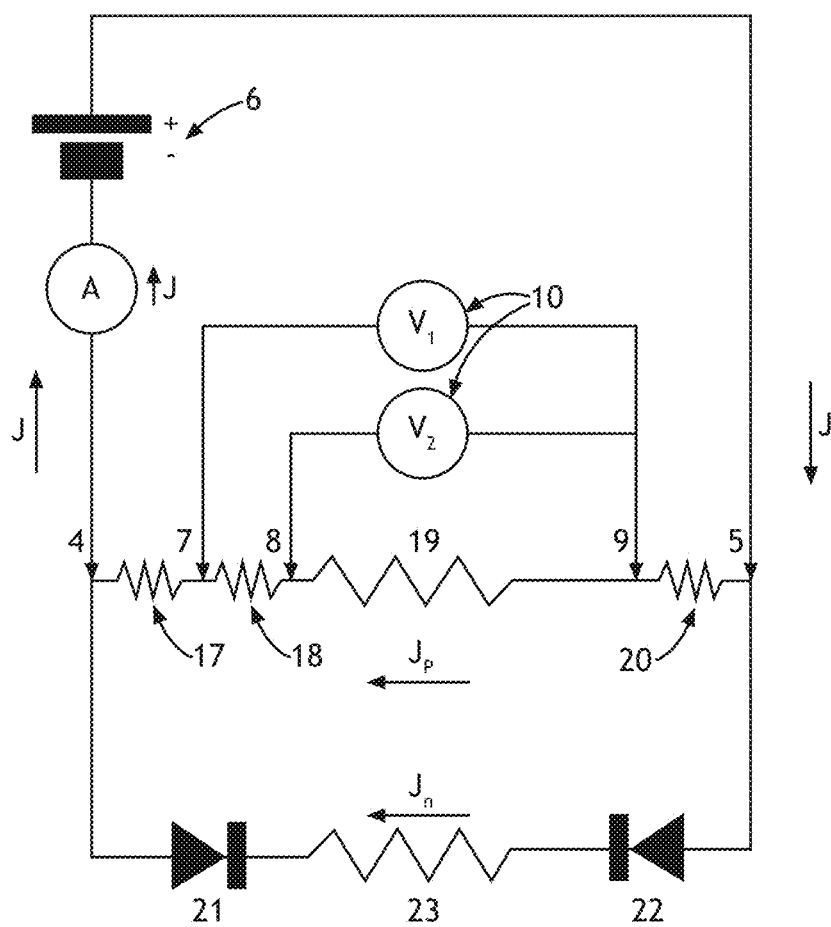
FIG. 27 is a simplified equivalent circuit of the current flow shown in FIG. 26.

FIG. 27 depicts the effective resistors 17, 18, 19, 20 of the p-layer 13 formed between probes 4 and 7, 7 and 8, 8 and 9, 9 and 5, respectively. Also shown in FIG. 27 are back-to-back diodes 21 and 22 simulating two p-n junctions underneath the two current probes 4 and 5. Resistor 23 represents the effective resistance of n-layer 15 between probes 4 and 5. The current $J=J_n+J_p$, where $J_p$ represents the current through p-layer 13 and $J_n$ represents the current through n-layer 15.

Figure 28:
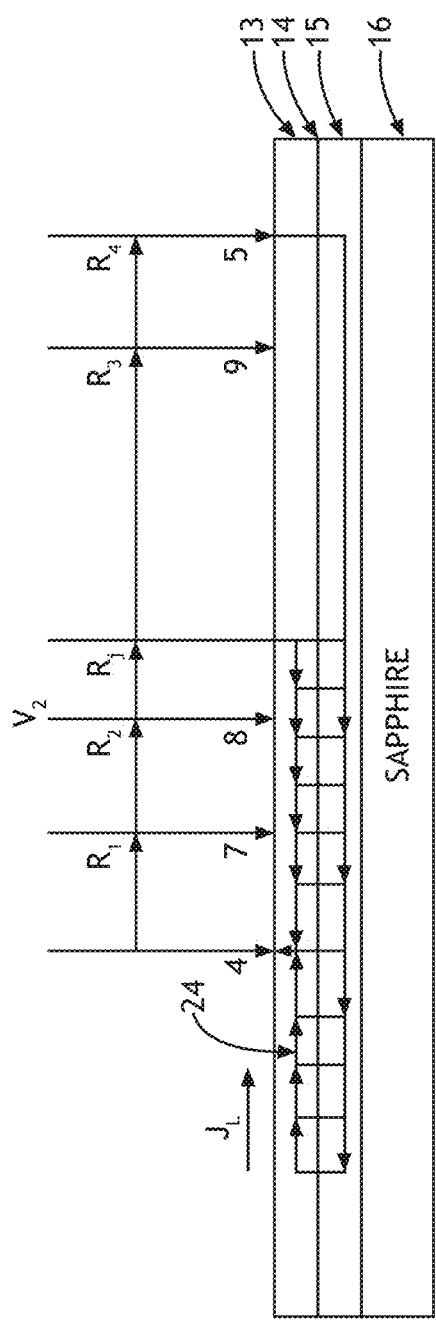
FIG. 28 is an illustration depicting the current flow shown in FIG. 26.

The position of probes 4, 5, 7, 8, and 9, as well as the current flow 24 between probes 4 and 5 through p-layer 13, p-n junction layer 14, and n-layer 15, are shown in FIG. 28. The distances of probes 7, 8, 9, and 5 from probe 4 are denoted as $r_1, r_2, r_3$, and $r_4$, respectively. It is noted that since at probe 4 applied reverse bias on p-n junction layer 14 diode 21, the current flows through p-layer 13 around probe 4 is distributed in an area of p-n structure with radius $r_j$.

Utilizing the mathematical notations defined above, the lateral current $J_L(r)$ may be calculated based on the lateral electric field at the edge of probe 4 and the p-layer 13 sheet resistance $R_{sp}$. More specifically, the lateral current may be determined using formula:

$$J_L(r) = -\frac{2\pi r}{R_{SP}} \frac{dV}{dr}$$

The lateral current in the p-layer 13 crossing a circular boundary centered at probe 4 with radius $r<r_1$ may be determined as:

$$J_L(r_1) \cong -\pi \frac{r_2+r_1}{R_{sp}} \frac{V_2-V_1}{r_2-r_1}$$

Furthermore, the current $J_{norm}$ parallel to the surface normal crossing through an area defined by the above mentioned circular boundary surrounding probe 4 with $r<r_1$ and density of leakage current, j, may be determined as:

$$J_{norm} = J - J_L$$

$$j \cong J_{norm}/\pi r_1^2$$

It is to be understood that the various probes utilized by the apparatus 1 shown in FIG. 25 are merely exemplary. It is contemplated that the placement of the various probes may vary without departing from the spirit and scope of the present disclosure.

Figure 29:
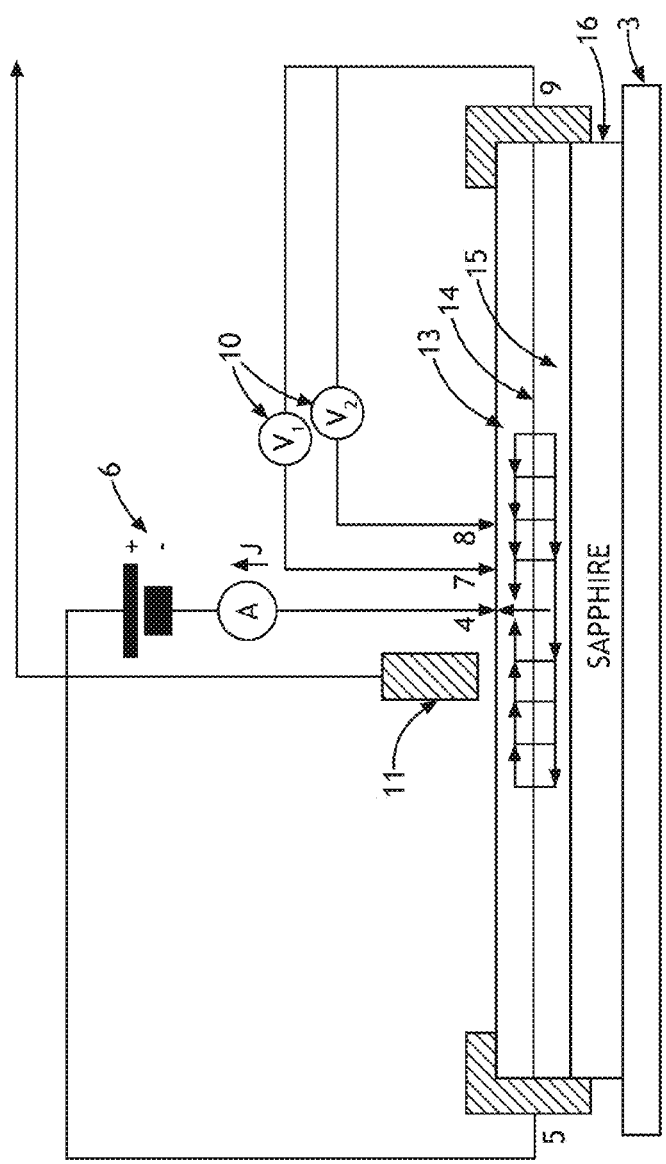
FIG. 29 is an illustration depicting a variant of the measurement apparatus shown in FIG. 25.
Figure 30:
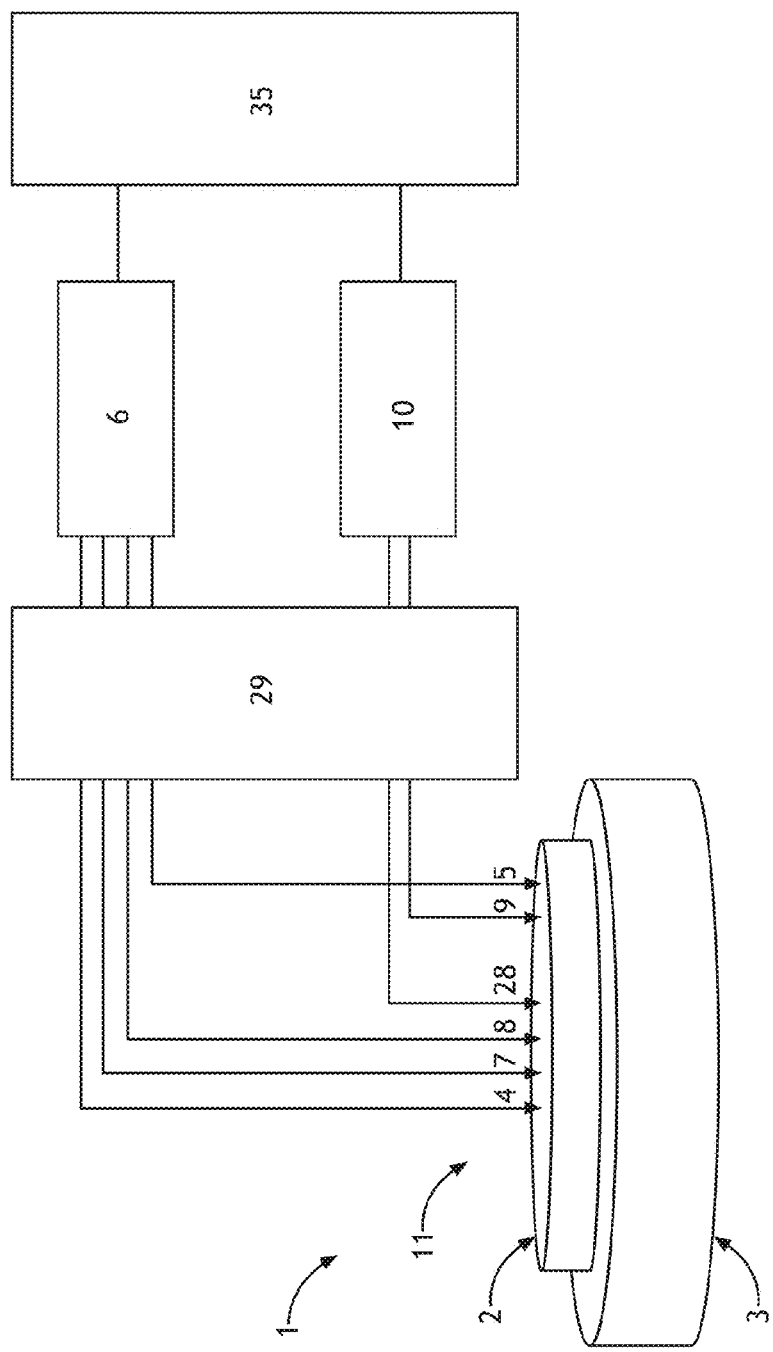
FIG. 30 is an illustration depicting another variant of the measurement apparatus, wherein a four point probe technique is utilized for sheet resistance measurement.

For instance, referring to FIG. 29, a variant of the apparatus 1 is shown. Instead of connecting to the p-layer 13, direct contact of probes 5 and 9 are provided to the n-layer 15 at the sides, as well as the edges and the top surface of the wafer 2. Another variant of the apparatus 1 is shown in FIG. 30. It is noted that an additional probe 28 and an electrical multiplexor 29 are utilized to form a four point probe together with probes 4, 7, and 8. As previously described, probes 4, 7, 8, and 28 can be used for measurements of sheet resistance $R_{sp}$, eliminating the need for a dedicated sheet resistance measurement probe. Furthermore, applying current between probes 4 and 5 and measuring potential difference between probes 7 and 9 and between probes 8 and 9 may allow the reverse biased I-V curve to be obtained.

Figure 31:
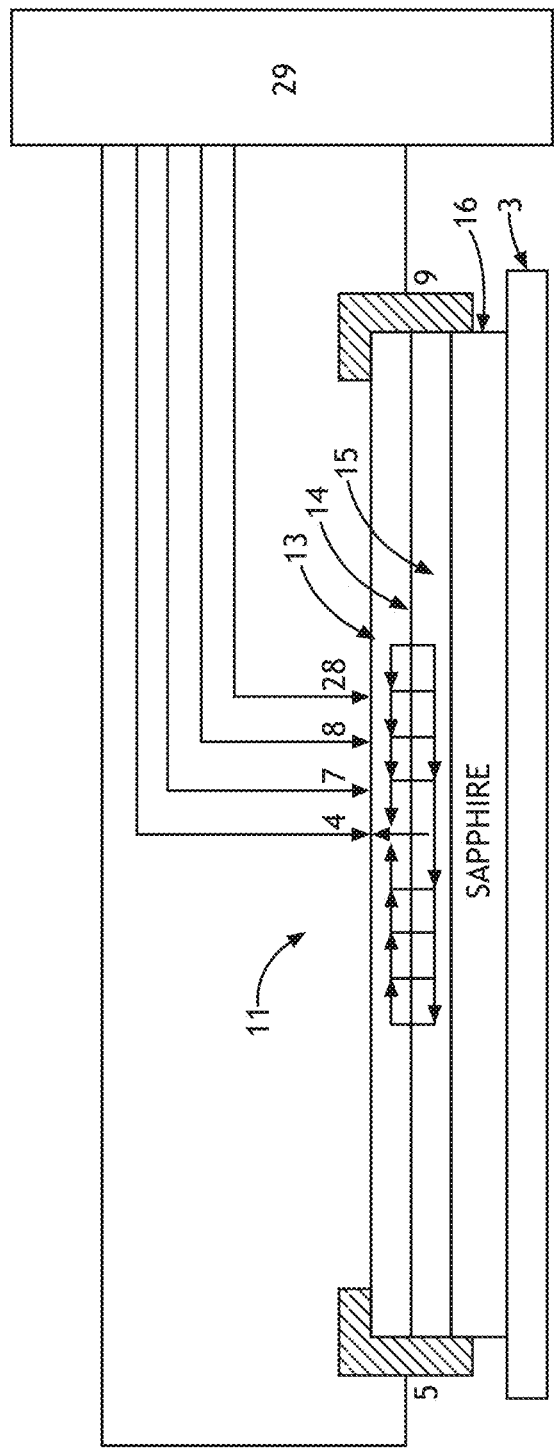
FIG. 31 is an illustration depicting another variant of the measurement apparatus.

Referring to FIG. 31, another variant of the apparatus 1 is shown. Direct contact of probes 5 and 9 are configured in a similar manner as those depicted in FIG. 29. In addition, probe 28 is used in conjunction with probes 4, 7, and 8 for measurements of sheet resistance $R_{sp}$ similar to the probe 28 depicted in FIG. 30.

Figure 32:
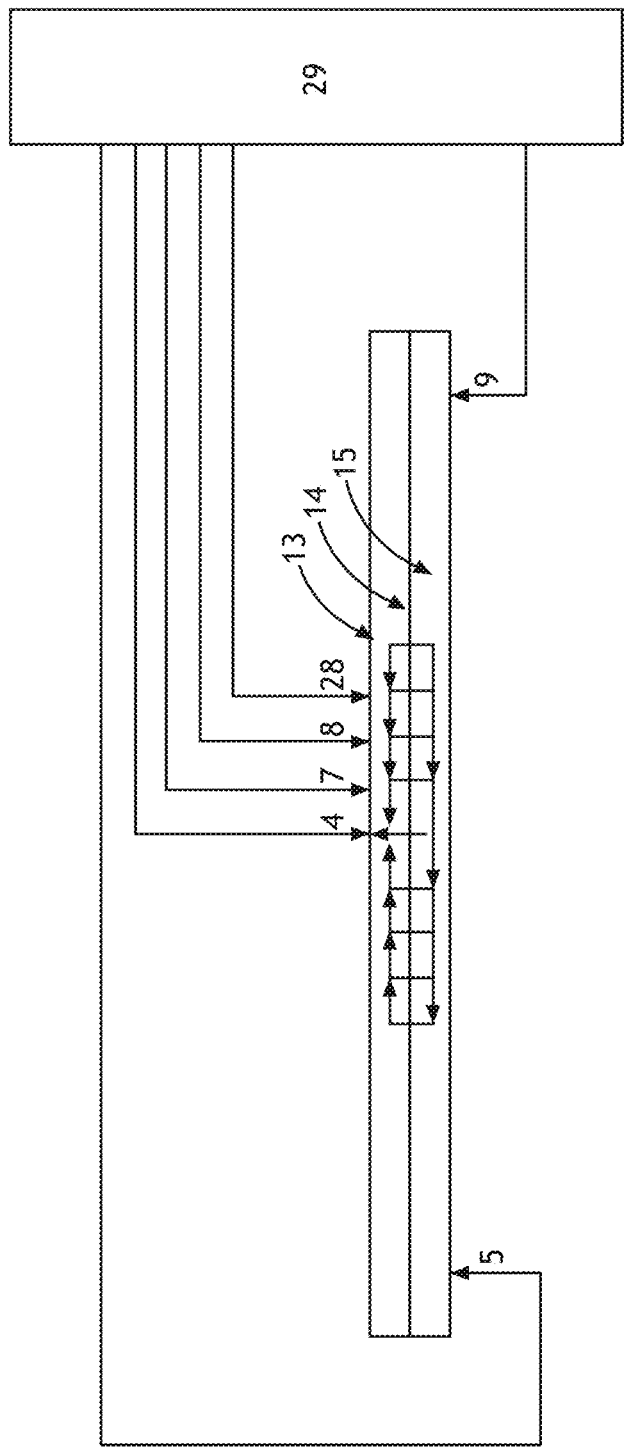
FIG. 32 is an illustration depicting still another variant of the measurement apparatus.

FIG. 32 shows still another variant of the apparatus. It is noted that the p-n junction layer 14 may be present without the dielectric (sapphire) substrate 16. For such wafers 2, probes 5 and 9 may directly contact the bottom of the p-n junction layer 14 from the back side of the wafer 2. This variant of the apparatus 1 may be used for leakage measurements for monitoring wafers 2 used in process control of various fabrications processes such as image sensors and the like.

Figure 33:
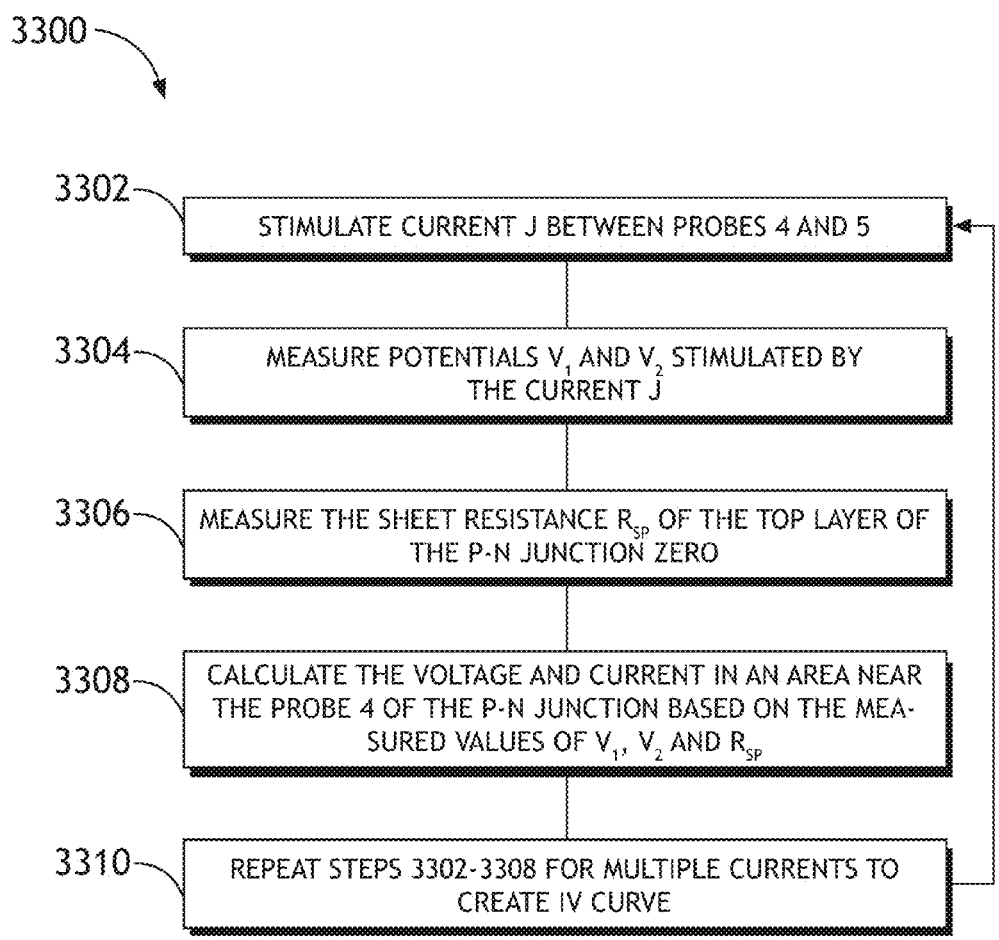
FIG. 33 is a flow depicting a method for obtaining I-V curve of the p-n junction, wherein the lateral current is calculated and taken into consideration.

FIG. 33 is a flow diagram depicting a method 3300 for taking measurements utilizing the apparatus described above. More specifically, a current J is stimulated between probes 4 and 5 in step 3302. Measurements of potentials $V_1$ and $V_2$ stimulated by the current J are taken in step 3304 using probes 7, 8, and 9. In addition, the measurement of the sheet resistance $R_{sp}$ of the top layer of the p-n junction layer 14 is taken in step 3306. As mentioned previously, the sheet resistance $R_{sp}$ may be measured using a dedicated sheet resistance probe 11 or using probes 4, 7, 8, and 28. Based on the measured values of $V_1$, $V_2$ and $R_{sp}$, the voltage and current in an area near the probe 4 of the p-n junction layer 14 may be calculated in step 3308 utilizing the equations described above.

It is contemplated that this process may be repeated for a plurality of different currents J under reverse as well as forward bias conditions to obtain the I-V curve in step 3310. It is also contemplated that the method 3300 may be applicable under forward and/or reverse-bias conditions, allowing the current-voltage characteristics of the p-n junction layer 14 to be determined under either or both conditions.

It is contemplated that the advantages provided by the methods and systems in accordance with embodiments of the present disclosure include the abilities to control (or minimize) the lateral current, as well as the abilities to take into account the lateral current for more accurate measurements of leakage current, I-V curves, as well as other measurements that require known current density such as capacitance measurements using AC rather than, or in addition to, DC current source. It is noted that the methods and systems in accordance with embodiments of the present disclosure may also be utilized for wafers that include GaInN LED structures grown on sapphire, which may only allow contacts to the top surface and sides of the wafer 2.

The methods and systems in accordance with embodiments of the present disclosure may also be useful for monitoring of leakage current in implant layers for CCD or CMOS imagers. For instance, the methods and systems in accordance with embodiments of the present disclosure may be particularly useful for measurements of leakage current in GaInN LED structures after metalorganic chemical vapor deposition (MOCVD) and anneal processes. Leakage current under reverse bias $V<=-5V$ in these structures can depend on the concentration of dislocations that may also be responsible for degradation of GaInN LEDs. Low current (e.g., about j=1 to 10 $\mu A/mm^2$) forward-voltage can also be an indicator for GaInN LED reliability and early stage accurate measurements can enable MOCVD process control.

It is to be understood that the p-n junctions given as examples in the present disclosure are specific to GaInN LED structures where the p-layer is on top and the n-layer is on the bottom. However, such depictions are exemplary, and p-n junctions may be structured in various other ways without departing from the spirit and scope of the present disclosure. For instance, an n-layer may be formed on top of a p-type silicone substrate, in which case the polarity of the electronics may be reversed to properly bias. In addition, it is also to be understood that the methods and systems in accordance with embodiments of the present disclosure are applicable to other types of junctions without departing from the spirit and scope of the present disclosure. Such junctions may include p-i-n structures and heterojunctions including multi-quantum well structures such as LEDs and laser diodes.

It is to be understood that the present disclosure may be implemented in forms of a software/firmware/hardware package. Such a package may be a computer program product which employs a computer-readable storage medium/device including stored computer code which is used to program a computer to perform the disclosed function and process of the present disclosure. The computer-readable medium may include, but is not limited to, any type of conventional floppy disk, optical disk, CD-ROM, magnetic disk, hard disk drive, magneto-optical disk, ROM, RAM, EPROM, EEPROM, magnetic or optical card, or any other suitable media for storing electronic instructions.

The methods disclosed may be implemented as sets of instructions, through a single production device, and/or through multiple production devices. Further, it is understood that the specific order or hierarchy of steps in the methods disclosed are examples of exemplary approaches. Based upon design preferences, it is understood that the specific order or hierarchy of steps in the method can be rearranged while remaining within the scope and spirit of the disclosure. The accompanying method claims present elements of the various steps in a sample order, and are not necessarily meant to be limited to the specific order or hierarchy presented.

It is believed that the system and method of the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory.

What is claimed is:

1. An apparatus, comprising:
   a first probe configured for establishing an electrical connection with a surface of a first layer of a p-n junction, the established electrical connection covering an area of the surface of the first layer of the p-n junction optimized to minimize a lateral current;
   a second probe configured for electrically contacting both the first layer and a second layer forming the p-n junction;
   a measurement unit electrically connected to the first probe and the second probe, the measurement unit configured for measuring at least one of: a voltage between the first and second probes and a current between the first and second probes when the first and the second probes are stimulated;
   a guard loop configured for preventing the lateral current from the first probe; and
   wherein at least one of: a voltage and a current applied to the guard loop is adjustable based on a measured surface voltage differential between the first probe and the guard loop.

2. The apparatus of claim 1, wherein the first probe is a disc probe having a sufficiently large diameter to diminish the lateral current flow outside of the disc probe.

3. The apparatus of claim 1, wherein the area covered by the first probe is optimized for accuracy and spatial mapping resolution such that a ratio of the lateral current to a normal current under the first probe is within a required accuracy of density leakage current measurement.

4. The apparatus of claim 1, wherein the first probe is made from a conductive elastic polymer.

5. The apparatus of claim 1, wherein the first probe is mounted to a mechanical actuator to provide full compliance to angular offsets of the surface of the first layer of the p-n junction.

6. The apparatus of claim 1, further comprising:
   at least one voltage measurement probe configured for measuring a surface voltage at a location within the area of the surface covered by the first probe.

7. The apparatus of claim 6, wherein the at least one voltage measurement probe is a disc probe providing contact with the surface of the first layer of the p-n junction inside of an opening defined by the first probe.

8. The apparatus of claim 6, wherein the at least one voltage measurement probe is a non-contact probe placed near the surface of the first layer of the p-n junction inside of an opening defined by the first probe.

9. The apparatus of claim 6, wherein the first probe is a ring probe having a sufficiently large diameter to diminish the lateral current flow outside of the ring probe, and wherein the at least one voltage measurement probe is configured for measuring the surface voltage at an opening defined at a center of the ring probe.

10. The apparatus of claim 1, further comprising: a plurality of electrical contacts established between the first probe and the guard loop, the plurality of electrical contacts configured for measuring a surface voltage drop between the first probe and the guard loop.

11. The apparatus of claim 1, wherein the surface voltage differential is measured using at least one non-contact probe.

12. An apparatus, comprising:
   a first probe configured for establishing an electrical connection with a surface of a first layer of a p-n junction;
   a second probe configured for contacting the p-n junction;
   a plurality of voltage measurement probes configured for measuring a surface voltage drop;
   a guard loop configured for preventing a lateral current from the first probe, wherein at least one of a voltage and a current applied to the guard loop is adjustable based on the measured surface voltage drop; and
   a measurement unit electrically connected to the first probe and the second probe, the measurement unit configured for measuring at least one of: a voltage between the first and second probes and a current between the first and second probes when the first and second probes are stimulated.

13. The apparatus of claim 12, wherein the electrical connection established by the first probe covers an area of the surface of the first layer of the p-n junction optimized to minimize the lateral current.

14. The apparatus of claim 13, wherein the first probe is a disc probe having a sufficiently large diameter to diminish the lateral current flow outside of the disc probe.

15. The apparatus of claim 14, wherein the disc probe is made from a conductive elastic polymer.

16. The apparatus of claim 15, wherein the disc probe is mounted to a mechanical actuator and assembly to provide full compliance to angular offsets of the surface of the first layer of the p-n junction.

17. The apparatus of claim 12, wherein one of the plurality of voltage measurement probes is configured for measuring a surface voltage at a location within the area of the surface covered by the first probe.

18. The apparatus of claim 17, wherein the first probe is a ring probe having a sufficiently large diameter to diminish the lateral current flow outside of the ring probe, and wherein said one of the plurality of voltage measurement probes is configured for measuring the surface voltage at an opening defined at a center of the ring probe.

19. The apparatus of claim 12, wherein at least one of the plurality of voltage measurement probes is configured for measuring a surface voltage at a location between the first probe and the guard loop.

20. The apparatus of claim 12, wherein at least one of the plurality of voltage measurement probes is a vibrating non-contact probe.

21. An apparatus, comprising:
   a first probe configured for establishing an electrical connection with a surface of a first layer of a p-n junction;
   a second probe configured for contacting the p-n junction;
   a plurality of voltage measurement probes configured for measuring surface voltages at different distances away from the first probe when the first and second probes are stimulated;
   at least one additional probe configured for facilitating measurement of a sheet resistance of the first layer of the p-n junction; and
   a measurement unit configured for calculating a lateral current in proximity to the first probe based on the measured surface voltages at different distances away from the first probe and the measured sheet resistance.

22. The apparatus of claim 21, wherein the first probe, the plurality of voltage measurement probes, and the at least one additional probe jointly form a four point probe (4PP) for measuring the sheet resistance of the first layer of the p-n junction.

23. The apparatus of claim 21, wherein the at least one additional probe includes a non-contact junction photovoltage probe for measuring the sheet resistance of the first layer of the p-n junction.

24. The apparatus of claim 21, wherein the second probe is connected to a second layer of the p-n junction.

25. The apparatus of claim 21, wherein the lateral current [I] in proximity to the first probe is determined based on:
- a current J utilized to stimulate the first and the second probes;
- at least two measured surface voltages $V_1$ and $V_2$ measured at distances $r_1$ and $r_2$ away from the first probe, $r_1 < r_2$; and
- the measured sheet resistance Rsp.

26. The apparatus of claim 25, wherein a density of leakage current j in proximity to the first probe is determined as:

$$J_{norm} \cong J - \pi \frac{r_2 + r_1}{R_{sp}} \frac{V_2 - V_1}{r_2 - r_1}$$

$$j \cong J_{norm} / \pi r_1^2.$$

27. The apparatus of claim 25, wherein a voltage v in proximity to the first probe is determined as $V = V_1$.

* * * * *